US008222005B2

(12) United States Patent
Ruan et al.

(10) Patent No.: US 8,222,005 B2
(45) Date of Patent: Jul. 17, 2012

(54) METHOD FOR GENE IDENTIFICATION SIGNATURE (GIS) ANALYSIS

(75) Inventors: Yijun Ruan, Singapore (SG); Patrick Ng, Singapore (SG); Chialin Wei, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 571 days.

(21) Appl. No.: 10/664,234

(22) Filed: Sep. 17, 2003

(65) Prior Publication Data

US 2005/0059022 A1    Mar. 17, 2005

(51) Int. Cl.
  C12P 19/34   (2006.01)
  C12N 15/66   (2006.01)
  G01N 33/50   (2006.01)

(52) U.S. Cl. ............... 435/91.52; 435/91.2; 435/91.41; 435/91.53; 702/20

(58) Field of Classification Search .................. None
See application file for complete search history.

(56) References Cited

U.S. PATENT DOCUMENTS

| | | | |
|---|---|---|---|
| 4,766,072 A | 8/1988 | Jendrisak et al. | 435/91 |
| 6,054,276 A | 4/2000 | Macevicz | |
| 6,136,537 A | 10/2000 | Macevicz | |
| 6,143,528 A | 11/2000 | Hayashizaki | 435/91.1 |
| 6,303,308 B1 | 10/2001 | Halle et al. | |
| 6,383,743 B1 * | 5/2002 | Kinzler et al. | 435/6 |
| 6,410,243 B1 | 6/2002 | Wyrick et al. | |
| 6,498,013 B1 | 12/2002 | Velculescu et al. | 435/6 |
| 2002/0025561 A1 * | 2/2002 | Hodgson | 435/91.1 |
| 2002/0065609 A1 | 5/2002 | Ashby | |
| 2002/0102604 A1 | 8/2002 | Milne Edwards et al. | |
| 2003/0008290 A1 | 1/2003 | Velculescu et al. | |
| 2004/0146866 A1 | 7/2004 | Fu | |
| 2005/0059022 A1 | 3/2005 | Ruan et al. | |
| 2005/0255501 A1 * | 11/2005 | Ng et al. | 435/6 |

FOREIGN PATENT DOCUMENTS

| | | |
|---|---|---|
| EP | 0 761 822 B1 | 5/2003 |
| WO | WO 01/48247 A2 | 7/2001 |
| WO | WO 02/10438 A3 | 2/2002 |
| WO | WO 03/106672 A2 | 12/2003 |
| WO | WO 2004/050918 A1 | 6/2004 |
| WO | 2006003721 A1 | 1/2006 |

OTHER PUBLICATIONS

New England Biolabs 2000/2001 Catalog, p. 196.*
Belfort, 1997, Nucleic Acid Research, vol. 25, pp. 3379-3388.*
Saha, 2002, Nature Biotechnology, vol. 19, pp. 508-512.*
Tucholski, 1995, Gene, vol. 157, pp. 87-92.*
GenBank accession No. X65305.2, Jan. 2000.*
Result 24 of search of SEQ ID No.18 in GenEmbl.*
"Enzymes with Nonpalindromic Sequences," New England BioLabs (neb.com/nebecomm/tech_reference/restriction_enzymes/nonpalindromes.asp), 6 pages, date not available.*

(Continued)

Primary Examiner — Diana Johannsen
(74) Attorney, Agent, or Firm — Rothwell, Figg, Ernst & Manbeck PC

(57) ABSTRACT

An isolated oligonucleotide comprising at least one ditag, wherein the ditag comprises two joined first and second sequence tags, wherein the first tag comprises the 5'-terminus sequence and the second tag comprises the 3'-terminus sequence of a nucleic acid molecule or a fragment thereof. The ditag analysis is useful for gene discovery and genome mapping.

22 Claims, 10 Drawing Sheets

GIS analysis (bacterial transformation approach)

OTHER PUBLICATIONS

"Single cutters, pzero," NewEngland BioLabs (tools.neb.com/NEBcutter2/listbycuts.php?name=07fc4160-pzero&numcuts-1), 2 pages, date not available.*

Jongeneel et al., "Comprehensive sampling of gene expression in human cell lines with massively parallel signature sequencing", Proc. Natl. Acad. Sci, 100:4702-4705, 2003.

Velculescu et al., "Serial analysis of gene expression", Science, 270:484-487, 1995.

Saha et al., "Using the transcriptome to annotate the genome", Nature Biotechnology, 20:508-512, 2002.

Mao et al., "In vitro cloning of complex mixtured of DNA on microbeads: Physical separation of differentially expressed cDNAs", Proc. Natl. Acad. Sci, 97:1665-1670, 20, 1999.

Brenner et al., "Gene expression analysis by massively parallel signature sequencing (MPSS) on microbead arrays", Nature Biotechnology, 18:630-634, 20, 2000.

Adams et al., "Complementary DNA sequencing: Expressed sequence tags and Human Genome Project", Science, 252:1651-1656, 1991.

Mathupala S.P. et al., "'In-gel' purified ditags direct synthesis of highly efficient SAGE libraries," *BMC Genomics*, Aug. 1, 2002, pp. 20-24, vol. 3.

Wei, C.L. et al., "5' Long serial analysis gene expression (LongSAGE) and 3' LongSAGE for transcriptome characterization and genome annotation," *Proc. Natl. Acad. Sci USA*, Aug. 10, 2004, pp. 11701-11706, vol. 101, No. 32.

Brenner, Sydney, "Gene expression analysis by massively parallel signature sequencing (MPSS) on microbead arrays," *Nature Biotechnology*, Jun. 2000, pp. 630-634, vol. 18, No. 6. Nature Pub. Co., New York, NY.

Ng, Patrick, et al., "Gene identification signature (GIS) analsis for transcriptome characterization and genome annotation," *Nature Methods*, Feb. 2005, pp. 105-111, vol. 2, No. 2.

Ruan, Yijun, et al., "Interrogating the transcriptome," *TRENDS in Biotechnology*, Jan. 2004, pp. 23-30, vol. 22, No. 1. Elsevier, Cambridge, GB.

Saha, Saurabh, et al., "Using the transcriptome to annotate the genome," *Nature Biotechnology*, May 2002, pp. 508-512, vol. 19, No. 5.

Velculescu, Victor E., et al., "Serial Analysis of Gene Expression," *Science*, Oct. 20, 1995, pp. 484-487, vol. 270, No. 5235. American Association for the Advancement of Science, U.S.

Yamamoto, Mikio, et al., "Use of serial analysis of gene expression (SAGE) technology," *Journal of Immunological Methods*, Apr. 1, 2001, pp. 45-66, vol. 250, No. 1-2. Elsevier B.V., Amsterdam, NL.

Kaeser, et al., Chromatin immunoprecipitation analysis fails to support the latency model for regulation of p53 DNA binding activity in vivo, PNAS, 99(1): 95-100 (Jan. 8, 2002).

Alam, et al., "A novel vector for the expression of SCR domains in insect cells," Journal of Immunological Methods, 293: 107-113 (2004).

Lieb, et al., "Promoter-specific binding of Rap1 revealed by genome-wide maps of protein-DNA association," Nature Genetics, 28(4): 327-334 (Aug. 2001).

Oren, "Decision making by p53: life, death and cancer," Cell Death and Differentiation, 10: 431-442 (2003).

Ren, et al., "Genome-Wide Location and Function of DNA Binding Proteins," Science, 290: 2306-2309(Dec. 22, 2000).

Margulies, et al., "Genome sequencing in microfabricated high-density picolitre reactors," Nature, 437: 376-380 (Sep. 15, 2005) (with one page Corrigendum dated May 4, 2006).

Li, et al., "Alteration of the Cleavage Distance of Fok I Restriction Endonuclease by Insertion Mutagenesis," PNAS 90: 2764-2768, 1993.

Strausberg, et al., "The Mammalian Gene Collection," Science, 286: 455-457 (1999).

www.Invitrogen.com/content/sfs/vectors/pzero1_rest.text, Feb. 23, 2007, 7 pages.

Iyer, et al., "Genomic binding sites of the yeast cell-cycle transcription factors SBF and MBF," Nature, 409(6819): 533-538 (Jan. 25, 2001).

Klug, et al., "All you wanted to know about SELEX," Molecular Biology Reports, 20: 97-107 (1994).

Zhang, Z.H. et al., "Mapping of transcription start sites in *Saccharomyces cerevisiae* using 5' SAGE". Nucleic Acids Res., vol. 33(9): 2838-2851, 2005.

Chum, Winnie W.Y. et al., "Modification of LongSAGE for obtaining and cloning long concatemers", BioTechniques, vol. 39(5): 637-640, 2005.

Taverner, et al., "Identifying transcriptional targets," Genome Biology, 5(3): 210.1-210.7 (2004).

Roulet et al., "High-throughput SELEX-SAGE method for quantitative modeling of transcription-factor binding sites," Nature Biotechnology, 20: 831-835 (Aug. 2002).

Moncke-Buchner et al., "Counting CAG repeats in the Huntington's disease gene by restriction endonuclease EcoP15I cleavage," Nucleic Acids Research, 30(16): e83, pp. 1-7 (2002).

Peters et al., "Transcriptome PETs: A genome's best friends", Nature Methods, vol. 2, No. 2, Feb. 2005, pp. 93-94.

Stratagene Catalogue, "pBIuscript® II Phagemid Kits," pp. 27-28 and 313, 1993, XP002905202.

Office Action dated Sep. 26, 2011, Canadian Intellectual Property Office, Application No. 2,538,137, Agency for Science, Technology and Research, Method for Gene Identification Signature (GIS) Analysis, 4 pages.

* cited by examiner

FIGURE 10
pGIS1 sequence

```
                    NotI
         XhoI              MmeI
    EcoRI            BamHI
    -------          ------
  1  GGGCGAATTC TCGAGCGGCC GCGGATCCGA CGAGAGCGCC TGCGTACGGC TCGCCGCGGT GGCTGGCGCT ACTTCGGAGG AGCCCGACGC GGCGCGGTCG
     CCCGCTTAAG AGCTCGCCGG CGCCTAGGCT GCTCTCGCGG ACGCATGCCG AGCGGCGCCA CCGACCGCGA TGAAGCCTCC TCGGGCTGCG CCGCGCCAGC

101  TTTTTATACA TTCCCGCGCG GAGGCAACGG AAGGGCGGGG CGCCTCGTGA GAGGTCACAG GCTCTGTTGT CATGAAGGTG AAAATTAAAT
     AAAAATATGT AAGGGCGCGC CTCCGTTGCC TTCCCGCCCC GCGGAGCACT AATCCGCGCC CTCCAGTGTC CGAGACAACA GTACTTCCAC TTTTAATTTA
     MmeI
     ------
201  GTTGGAATGG TGTGGCCACT TGGCTCTGGG TAGCCAATGA TGAGAACTGC GGCATCTGCA GGATGGCGTT TAATGGCTGC TGTCCAGACT GTAAGGTGCC
     CAACCTTACC ACACCGGTGA ACCGAGACCC ATCGGTTACT ACTCTTGACG CCGTAGACGT CCTACCGCAA ATTACCGACG ACAGGTCTGA CATTCCACGG

301  TGGTGATGAC TGCCCCCTCG TGTGGGACA GTGCTCCCAC TGCTTCCACA TGCACTGCAT CCTCAAGTGG CTGAATGCGC AGCAGGTGCA GCAGCACTGC
     ACCACTACTG ACGGGGGAGC ACACCCCTGT CACGAGGGTG ACGAAGGTGT ACGTGACGTA GGAGTTCACC GACTTACGCG TCGTCCACGT CGTCGTGACG

401  CCCATGTGTC GCCAGGAGTG GAAGTTCAAA GAGTGAAGCC CGTGCCGTGC CACTTCCCTC TCCTGTGCTG TGCCAGGCTC AGCCCCTTCC CTCCCCTCCC
     GGGTACACAG CGGTCCTCAC CTTCAAGTTT CTCACTTCGG GCACGGCACG GTGAAGGGAG AGGACACGAC ACGGTCCGAG TCGGGGAAGG GAGGGAGGGG

501  TCCCCCAGAT ACAGCACCCC AAGTCCCCTC CACACAGCAC AGTGGTGCCC AGAGATCTCG GTCTGTGCCG GGGACAAGGA TGCTTTCTGT TTGGCTGGGA
     AGGGGGTCTA TGTCGTGGGG TTCAGGGGAG GTGTGTCGTG TCACCACGGG TCTCTAGAGC CAGACACGGC CCCTGTTCCT ACGAAAGACA AACCGACCCT
                                                                                                         MmeI
                                                                                                         ------
                                                                                                BamHI
                                                                                                ------
601  CAAGGTTGAA AGGAGCTTTG CTGACTGTTT TGTTTTCCCA TCACATTGAC ACTTTATTCA ATAAGTAAAA CTCATTACAG TTCCAAGTCG GATCCTGGGT
     GTTCCAACTT TCCTCGAAAC GACTGACAAA ACAAAAGGGT AGTGTAACTG TGAAATAAGT TATTCATTTT GAGTAATGTC AAGGTTCAGC CTAGGACCCA
     SalI
     ----
701  CGACCTGCAG GCATGCAAGC TTGAGTATTC TATAGTGTCA CCTAAATAGC TTGGCGTAAT CATGGTCATA GCTGTTTCCT GTGTGAAATT GTTATCCGCT
     GCTGGACGTC CGTACGTTCG AACTCATAAG ATATCACAGT GGATTTATCG AACCGCATTA GTACCAGTAT CGACAAAGGA CACACTTTAA CAATAGGCGA

801  CACAATTCCA CACAACATAC GAGCCGGAAG CATAAAGTGT AAAGCCTGGG GTGCCTAATG AGTGAGCTAA CTCACATTAA TTGCGTTGCG CTCACTGCCC
     GTGTTAAGGT GTGTTGTATG CTCGGCCTTC GTATTTCACA TTTCGGACCC CACGGATTAC TCACTCGATT GAGTGTAATT AACGCAACGC GAGTGACGGG

901  GCTTTCCAGT CGGGAAACCT GTCGTGCCAG CTGCATTAAT GAATCGGCCA ACGCGCGGGG AGAGGCGGTT TGCGTATTGG GCGCTCTTCC GCTTCCTCGC
     CGAAAGGTCA GCCCTTTGGA CAGCACGGTC GACGTAATTA CTTAGCCGGT TGCGCGCCCC TCTCCGCCAA ACGCATAACC GCGAGAAGG CGAAGGAGCG

1001 TCACTGACTC GCTGCGCTCG GTCGTTCGGC TGCGGGCAGC GGTATCAGCT CACTCAAAGG CGGTAATACG GTTATCCACA GAATCAGGGG ATAACGCAGG
     AGTGACTGAG CGACGCGAGC CAGCAAGCCG ACGCCGCTCG CCATAGTCGA GTGAGTTTCC GCCATTATGC CAATAGGTGT CTTAGTCCCC TATTGCGTCC

1101 AAAGAACATG TGAGCAAAAG GCCAGCAAAA GGCCAGGAAC CGTAAAAAGG CCGCGTTGCT GGCGTTTTTC GATAGGCTCC GCCCCCCTGA CGAGCATCAC
     TTTCTTGTAC ACTCGTTTTC CGGTCGTTTT CCGGTCCTTG GCATTTTTCC GGCGCAACGA CCGCAAAAAG CTATCCGAGG CGGGGGGACT GCTCGTAGTG

1201 AAAAATCGAC GCTCAAGTCA GAGGTGGCGA AACCCGACAG GACTATAAAG ATACCAGGCG TTTCCCCCTG GAAGCTCCCT CGTGCGCTCT CCTGTACCGA
     TTTTTAGCTG CGAGTTCAGT CTCCACCGCT TTGGGCTGTC CTGATATTTC TATGGTCCGC AAAGGGGGAC CTTCGAGGGA GCACGCGAGA GGACATGGCT

1301 CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
     GGGACGGCGA ATGGCCTATG GACAGGCGGA AAGAGGGAAG CCCTTCGCAC CGCGAAAGAG TATCGAGTGC GACATCCATA GAGTCAAGCC ACATCCAGCA

1401 TCGCTCCAAG CTGGGCTGTG TGCACGAACC CCCCGTTCAG CCCGACCGCT GCGCCTTATC CGGTAACTAT CGTCTTGAGA CCAACCCGGT AAGACACGAC
     AGCGAGGTTC GACCCGACAC ACGTGCTTGG GGGGCAAGTC GGGCTGGCGA CGCGGAATAG GCCATTGATA GCAGAACTCT GGTTGGGCCA TTCTGTGCTG

1501 TTATGCCGAC TGGCAGCAGC CACTGGTAAC AGGATTAGCA GAGCGAGGTA TGTAGGCGGT GCTACAGAGT TCTTGAAGTG GTGGCCTAAC TACGGCTACA
     AATAGCGGTG ACCGTCGTCG GTGACCATTG TCCTAATCGT CTCGCTCCAT ACATCGCCA CGATGTCTCA AGAACTTCAC CACCGGATTG ATGCCGATGT

1601 CTAGAAGGAC AGTATTTGGT ATCTGCGCTC TGCTGAAGCC AGTTACCTTC GGAAAAAGAG TTGGTAGCTC TTGATCCGGC AAACAAACCA CCGCTGGTAG
     GATCTTCCTG TCATAAACCA TAGACGCGAG ACGACTTCGG TCAATGGAAG CCTTTTTCTC AACCATCGAG AACTAGGCCG TTTGTTTGGT GGCGACCATC

1701 CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
     GCCACCAAAA AAACAAACGT TCGTCGTCTA ATGCGCGTCT TTTTTTCCTA GAGTTCTTCT AGGAAACTAG AAAAGATGCC CCAGACTGCG AGTCACCTTG

1801 GAAAACTCAC GTTAAGGGAT TTTGGTCATG AGATTATCAA AAAGGATCTT CACCTAGATC CTTTTAAATT AAAAATGAAG TTTTAAATCA ATCTAAAGTA
     CTTTTGAGTG CAATTCCCTA AAACCAGTAC TCTAATAGTT TTTCCTAGAA GTGGATCTAG GAAAATTTAA TTTTTACTTC AAAATTTAGT TAGATTTCAT

1901 TATATGAGTA AACTTGGTCT GACAGTTACC AATGCTTAAT CAGTGAGGCA CCTATCTCAG CGATCTGTCT ATTTCGTTCA TCCATAGTTG CCTGACTCCC
     ATATATCTCAT TTGAACCAGA CTGTCAATGG TTACGAATTA GTCACTCCGT GGATAGAGTC GCTAGACAGA TAAAGCAAGT AGGTATCAAC GGACTGAGGG

2001 CGTCGTGTAG ATAACTACGA TACGGGAGGG CTTACCATCT GGCCCCAGTG CTGCAATGAT ACCGCGAGAC CCACGCTCAC CGGCTCCAGA TTTATCAGCA
     GCAGCACTAT TATTGATGCT ATGCCCTCCC GAATGGTAGA CCGGGGTCAC GACGTTACTA TGGCGCTCTG GGTGCGAGTG GCCGAGGTCT AAATAGTCGT

2101 ATAAACCAGC CAGCCGGAAG GGCCGAGCGC AGAAGTGGTC CTGCAACTTT ATCCGCCTCC ATCCAGTCTA TTAATTGTTG CCGGGAAGCT AGAGTAAGTA
     TATTTGGTCG GTCGGCCTTC CCGGCTCGCG TCTTCACCAG GACGTTGAAA TAGGCGGAGG TAGGTCAGAT AATTAACAAC GGCCCTTCGA TCTCATTCAT

2201 GTTCGCCAGT TAATAGTTTG CGCAACGTTG TTGGCATTGC TACAGGCATC GTGGTGTCAC GCTCGTCGTT TGGTATGGCT TCATTCAGCT CCGGTTCCCA
     CAAGCGGTCA ATTATCAAAC GCGTTGCAAC AACCGTAACG ATGTCCGTAG CACCACAGTG CGAGCAGCAA ACCATACCGA AGTAAGTCGA GGCCAAGGGT

2301 ACGATCAAGG CGAGTTACAT GATCCCCCAT GTTGTGCAAA AAAGCGGTTA GCTCCTTCGG TCCTCCGATC GTTGTCAGAA GTAAGTTGGC CGCAGTGTTA
     TGCTAGTTCC GCTCAATGTA CTAGGGGGTA CAACACGTTT TTTCGCCAAT CGAGGAAGCC AGGAGGCTAG CAACAGTCTT CATTCAACGG GCGTCACAAT

2401 TCACTCATGG TTATGGCAGC ACTGCATAAT TCTCTTACTG TCATGCCATC CGTAAGATGC TTTTCTGTGA CTGGTGAGTA CTCAACCAAG TCATTCTGAG
     AGTGAGTACC AATACCGTCG TGACGTATTA AGAGAATGAC AGTACGGTAG GCATTCTACG AAAAGACACT GACCACTCAT GAGTTGGTTC AGTAAGACTC

2501 AATAGTGTAT GCGGCGACCG AGTTGCTCTT GCCCGGCGTC AATACGGGAT AATACCGCGC CACATAGCAG AACTTTAAAA GTGCTCATCA TTGGAAAACG
     TTATCACATA CGCCGCTGGC TCAACGAGAA CGGGCCGCAG TTATGCCCTA TTATGCGCG GTGTATCGTC TTGAAATTTT CACGAGTAGT AACCTTTTGC

2601 TTCTTCGGGG CGAAAACTCT CAAGGATCTT ACCGCTGTTG AGATCCAGTT CGATGTAACC CACTCGTGCA CCCAACTGAT CTTCAGCATC TTTTACTTTC
     AAGAAGCCCC GCTTTTGAGA GTTCCTAGAA TGGCGACAAC TCTAGGTCAA GCTACATTGG GTGAGCACGT GGGTTGACTA GAAGTCGTAG AAAATGAAAG

2701 ACCAGCGTTT CTGGGTGAGC AAAAACAGGA AGGCAAAATG CCGCAAAAAA GGGAATAAGG GCGACACGGA AATGTTGAAT ACTCATACTC TTCCTTTTTC
     TGGTCGCAAA GACCCACTCG TTTTTGTCCT TCCGTTTTAC GGCGTTTTTT CCCTTATTCC CGCTGTGCCT TTACAACTTA TGAGTATGAG AAGGAAAAAG

2801 AATATTATTG AAGCATTTAT CAGGGTTATT GTCTCATGAG CGGATACATA TTTGAATGTA TTTAGAAAAA TAAACAAATA GGGGTTCCGC GCACATTTCC
     TTATAATAAC TTCGTAAATA GTCCCAATAA CAGAGTACTC GCCTATGTAT AAACTTACAT AAATCTTTTT ATTTGTTTAT CCCCAAGGCG CGTGTAAAGG

2901 CCGAAAAGTG CCACCTGACG TCTAAGAAAC CATTATTATC ATGACATTAA CCTATAAAAA TAGGCGTATC ACGAGGCCCT TTCGTCTCGC GCGTTTCGGT
     GGCTTTTCAC GGTGGACTGC AGATTCTTTG GTAATAATAG TACTGTAATT GGATATTTTT ATCCGCATAG TGCTCCGGGA AAGCAGAGCG CGCAAAGCCA

3001 GATGACGGTG AAAACCTCTG ACACATGCAG CTCCCGGAGA CGGTCACAGC TTGTCTGTAA CCGGATGCCG GGAGCAGACA AGCCCGTCAG GGCGCGTCAG
     CTACTGCCAC TTTTGGAGAC TGTGTACGTC GAGGGCCTCT GCCAGTGTCG AACAGACATT GGCCTACGGC CCTCGTCTGT TCGGGCAGTC CCGCGCAGTC

3101 CGGGTGTTGG CGGGTGTCGG GGCTGGCTTA ACTATGCGGC ATCAGAGCAG ATTGTACTGA GAGTGCACCA TATGCGGTGT GAAATACCGC ACAGATGCGT
     GCCCACAACC GCCCACAGCC CCGACCGAAT TGATACGCCG TAGTCTCGTC TAACATGACT TCACGTGGT ATACGCCACA CTTTATGGCG TGTCTACGCA

3201 AAGGAGAAAA TACCGCATCA GGCGCCATTC GCCATTCAGG CTGCGCAACT GTTGGGAAGG GCGATCGGTG CGGGCCTCTT CGCTATTACG CCAGCTGGCG
     TTCCTCTTTT ATGGCGTAGT CCGCGGTAAG CGGTAAGTCC GACGCGTTGA CAACCCTTCC CGCTAGCCAC GCCCGGAGAA GCGATAATGC GGTCGACCGC

3301 AAAGGGGGAT GTGCTGCAAG GCGATTAAGT TGGGTAACGC CAGGGTTTTC CCAGTCACGA CGTTGTAAAA CGACGGCCAG TGAATTGTAA TACGACTCAC
     TTTCCCCCTA CACGACGTTC CGCTAATTCA ACCCATTGCG GTCCAAAAG GGTCAGTGCT GCAACATTTT GCTGCCGGTC ACTTAACATT ATGCTGAGTG

3401 TATA
     ATAT
```

METHOD FOR GENE IDENTIFICATION SIGNATURE (GIS) ANALYSIS

FIELD OF THE INVENTION

The present invention relates generally to the field of gene and transcript expression and specifically to a method for the serial analysis of a large number of transcripts by identification of a gene signature (GIS) corresponding to defined regions within a transcript.

BACKGROUND OF THE INVENTION

One of the most important goals of the human genome project is to provide complete lists of genes for the genomes of human and model organisms. Complete genome annotation of genes relies on comprehensive transcriptome analysis by experimental and computational approaches. Ab initio predictions of genes must be validated by experimental data. An ideal solution is to clone all full-length transcripts and completely sequence them. This approach has gained recognition recently (Strausberg, R. L., et al., 1999, *Science*, 286: 455-457) and progress has been made (Jongeneel C. V., et al., 2003, Proc Natl Acad Sci USA. 100, 4702-4705). However, due to the complexity and immense volume of transcripts expressed in the various developmental stages of an organism's life cycle, complete sequencing analysis of all different transcriptomes still remains unrealistic.

To get around such a dilemma, a cDNA tagging strategy that obtains partial sequences that represent full transcripts has been developed and widely applied in determining genes and characterizing transcriptomes in the past decade.

In the expressed sequence tag (EST) approach, cDNA clones are sequenced from 5' and/or 3' nds (Adams, M., et al., 1991, *Science*, 252, 1651-1656). Each EST sequence read would generate on average a 500 bp tag per transcript. The number of same or overlapping ESTs would manifest the relative level of gene expression activity. Though EST is effective in identifying genes, it is prohibitively expensive to tag every transcript in a transcriptome. In practice, sequencing usually ceases after 10,000 or less ESTs are obtained from a cDNA library where millions of transcripts might be cloned.

To increase the efficiency in sequencing and counting large numbers of transcripts, Serial Analysis of Gene Expression (SAGE) ((Velculescu, V. E., et al., 1995, *Science*, 270, 484-487; Saha S, et al., 2002, *Nature Biotechnology*, 20, 508-12; U.S. Pat. No. 6,498,013; U.S. Pat. No. 6,383,743) and the recent Massively Parallel Signature Sequencing (MPSS) technique (Mao C., et al., 2000, *Proc Natl Acad Sci USA*, 97, 1665-1670; Brenner S, et al., 2000, *Nature Biotechnology*, 18, 630-634) were developed based on the fact that a short signature sequence (14-20 bp) of a transcript can be sufficiently specific to represent that gene.

Experimentally, short tags can be extracted from cDNA one tag per transcript. Such short tags can be efficiently sequenced either by a concatenation tactic (as for SAGE) or by a hybridization-based methodology for MPSS. For example, in SAGE, multiple tags are concatenated into long DNA fragments and cloned for sequencing. Each SAGE sequence readout can usually reveal 20-30 SAGE tags. A modest SAGE sequencing effort of less than 10,000 reads will have significant coverage of a transcriptome. Transcript abundance is measured by simply counting the numerical frequency of the SAGE tags.

With the availability of many assembled genome sequences in public databases, the use of a short tag strategy for transcriptome characterization is becoming popular (Jongeneel et al., 2003, *Proc. Natl. Acad. Sci. USA* 100: 4702-4705). In theory, short DNA tags of about 20 bp can be specifically mapped to a single location within a complex mammalian genome and uniquely represent a transcript in the content of whole transcriptome. However, in reality, there still exist a large number of "ambiguous" SAGE tags (14-21 bp) and MPSS tags (17 bp) that have multiple locations in a genome, and may be shared by many genes. Limited by the availability of type II restriction enzymes that can cut longer than 21 bp, the SAGE method currently can not generate any longer tags to improve specificity.

Further, SAGE and MPSS methods only produce a single signature per transcript in the middle of the gene. In view of the "internal" nature of the tag in a transcript, these methods provide only limited tag information.

Therefore, despite their usefulness in sequencing efficiency, the utility of methods such as SAGE or MPSS is severely undermined by their lack of specificity and consequent inconclusiveness.

There is a need in the art for more efficient methods which retain the sequencing efficiency and at the same time improve the use of the tagging strategy for transcriptome characterization and facilitate the annotation of genomes.

SUMMARY OF THE INVENTION

The present invention solves the problems mentioned above by providing two tags (a ditag) per nucleic acid molecule, therefore increasing the specificity of the tags to represent a nucleic acid molecule (for example a gene). The two tags are extracted from the 5' and 3' ends of the same nucleic acid molecule, and therefore ditags are more informative to reflect the structure of the nucleic acid molecules. Critically, the invention provides a method to link the 5' and 3' tags of the same nucleic acid molecule into a single ditag unit. Therefore, the pairs of 5' and 3' tags that represent the nucleic acid molecule can be easily recognized by simple sequencing analysis. The invention can be used for the identification of new genes, for the measure of transcript abundance in transcriptomes, for the annotation of genome sequences and at the same time enhancing sequencing efficiency.

In particular, the invention provides an isolated oligonucleotide comprising at least one ditag, wherein the ditag comprises two joined first and second sequence tags, wherein the first tag comprises the 5'-terminus sequence and the second tag comprises the 3'-terminus sequence of a nucleic acid molecule.

The oligonucleotide of the invention, further comprises at least two adapters flanking the ditag, wherein each adapter comprises at least one restriction site. In particular, each adapter comprises at least: a first restriction site proximal to the tag which is an asymmetric recognition site (for example, a homing endonuclease recognition site, or a type II recognition site) and at least a second restriction site. The second or further restriction site may be any restriction site known in the art may be used. For example, BamHI. Also, any asymmetric restriction site different from the first restriction site may be used. The recognition site for this enzyme however must be absent from the vector backbone after insertion of the ditag The nucleic acid molecule may be the full-length sequence of a gene or a fragment thereof. For example, RNA, mRNA, genomic DNA, full-length cDNA or cDNA.

The ditag may vary in nucleotide number. According to one embodiment, it is obtained by splicing the 5' terminus and the 3' terminus of a nucleic acid molecule in presence of at least one restriction enzyme and the size of the sequence tags is determined by the restriction enzyme used. Accordingly, the number of nucleotides of the ditag can vary according to the restriction enzyme used.

When MmeI is used, this enzyme recognizes a sequence inside each of the two adapters that flank the nucleic acid molecule which one intends to reduce, but cuts inside the nucleic acid molecule forming a tag comprising 19-21 nucleotides. Two such tags may be additionally processed by blunting and ligation to form a ditag comprising 34-38 nucleotides. The ditag is hence obtained by splicing together the 5' terminus and the 3' terminus of the same nucleic acid molecule.

The ditag of the invention can be of any size, preferably 12-60 bp.

The oligonucleotide may comprise a concatemer of ditags, for example 1 to 1000 ditags.

The invention also provides a vector comprising the oligonucleotide of the invention. In particular, the vector comprises at least a nucleic acid molecule and at least two adapters flanking the nucleic acid molecule, wherein each adapter comprises at least: a first restriction site which is a asymmetric restriction site (asymmetric restriction site is, for example, a homing endonuclease recognition site, or a type II recognition site) and at least a second restriction site (for example Bam HI), and the backbone of the vector does not comprise the asymmetric restriction site and the second or further restriction site. A preferable, asymmetric restriction site is the type II restriction site MmeI.

The invention also provides a vector having the sequence indicated in SEQ ID NO:18.

The invention further provides a cDNA library, wherein every cDNA clone comprises the at least one oligonucleotide of the invention.

According to another aspect, the invention also provides a method for preparing at least one oligonucleotide comprising at least one ditag comprising:
  producing at least one nucleic acid molecule;
  isolating the 5' terminus and the 3' terminus of the nucleic acid molecule or fragment thereof; and
  linking the 5' terminus and 3' terminus to create the at least one ditag.

In particular, it is provided a method for preparing at least one oligonucletide comprising at least one ditag comprising:
  producing at least one nucleic acid molecule flanked by two adapters;
  isolating the 5' terminus and the 3' terminus of the nucleic acid molecule; and
  linking the 5' terminus and 3' terminus to create the at least one oligonucleotide comprising at least one ditag flanked by the two adapters.

The nucleic acid molecule desired to be reduced in form of a ditag may be a full nucleic acid molecule or a portion inside the nucleic acid molecule.

The nucleic acid molecule may correspond to the full-length of a gene or fragment thereof.

The method may further comprise the step of determining the nucleotide sequence of the at least one ditag to detect gene expression.

According to a further aspect, the method of the invention may further comprise the steps of:
  determining the sequence of the at least one ditag; and
  comparing the ditag nucleotide sequence to a database comprising genomic sequences whereby matching 5' and 3' termini sequences are identified.

According to a particular embodiment, the invention provides a method comprising:
  producing at least one nucleic acid molecule, preferably a full-length cDNA, flanked by two adapters, wherein each adapter comprises at least one restriction site; splicing the 5' terminus and the 3' terminus of the nucleic acid molecule to produce at least one ditag by adding at least one restriction enzyme recognizing the recognition sites.

Preferably, each adapter comprises at least: a first restriction site which is an asymmetric restriction site and a second restriction site.

As restriction enzyme, any useful enzyme can be used. For example, a restriction enzyme recognizing two asymmetric recognition sites.

Asymmetric recognition site can be: i) homing endonuclease asymmetric recognition site sequences or ii) restriction endonuclease asymmetric cleavage sites sequences recognizable by type II restriction enzymes.

According to a particular embodiment, the splicing step is carried out by using MmeI (together with T4 DNA polymerase and T4 DNA ligase) and the ditag of 34-38 nucleotides, flanked by two adapters, is produced.

According to a further aspect, the ditag of any embodiment of the invention can be linked to other ditags to produce concatemers of ditag. For example, 1 to 1000 ditags.

According to another further aspect, it is provided a method for genome mapping, comprising:
  preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
  mapping each of the two tags of the at least one ditag on the genome; and
  defining the structural region of the corresponding gene on the genome map.

According to a still another aspect, the invention provides a method of gene discovery comprising:
  preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
  comparing the obtained at least one ditag with a genome map and/or a gene database;
  if the 5' and 3' termini tags of a ditag are matched to the genome sequence but not in known gene databases, then the detected ditags may represent new genes in the given genomes.

Such ditags can directly guide the process of recovering the full-length nucleic acid molecule corresponding to the newly identified genes.

It is also an aspect of the invention a method for recovering the full-length cDNA of new and/or other interesting genes comprising:
  preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA library;
  sequencing the obtained oligonucleotide ditag, preferably a large number of the obtained ditags;
  determining the ditag of interest (for example, based on biological aspects); and recovering the full-length cDNA corresponding to the ditag of interest from the parental full-length cDNA library.

Further, the invention also provides a method for quantifying the transcriptional activity of a gene comprising:
preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;
sequencing the obtained oligonucleotide ditag, preferably a large number of the obtained ditags;
determining the frequency of the sequenced ditag which corresponds to the transcriptional activity of the gene.

BRIEF DESCRIPTION OF THE FIGURES

FIG. 10 shows the double strand nucleotide sequence of pGIS1. The region between the restriction sites Not I and Sal I is the stuffer fragment that is removed during cloning. It is highlighted in bold and italic type. The single strand nucleotide sequence is also reported as SEQ ID NO:18. The region representing the stuffer fragment is between nucleotide 15 to 704 (both nucleotides included).

DETAILED DESCRIPTION OF THE INVENTION

The present invention provides a Gene Identification Signatures (GIS) and a GIS analysis method: useful, for example, for the rapid analysis of numerous transcripts in order to identify the overall pattern of transcript expression (transcriptome), for the selection and/or construction of cDNA and full-length cDNAs, tag sequencing, gene discovery, genome mapping and annotation. In general, the GIS and GIS analysis method according to the invention greatly facilitates the collection of gene information by experimental approach.

For the purpose of the present application, GIS means a ditag (also indicated as GIS ditag) or an oligonucleotide comprising at least one ditag, wherein the ditag comprises the 5' terminus (or end region) and the 3' terminus (or end region) of a nucleic acid molecule, which it is desired to reduce, "shrink" or represent.

The ditag is shorter than the original nucleic acid molecule from which it originates or which it represents. Preferably, the ditag must be much shorter than the original nucleic acid molecule. As consequence of the "shrinking", the ditag essentially comprises the 5' end region (also indicated as 5' tag) and 3' end region (also indicated as 3' tag) of the original nucleic acid molecule. Hence, the portion of the original nucleic acid molecule which is between or inside the 5' tag and 3' tag is not included in the ditag. The ditag according to the invention retains the most informative features of the original nucleic acid molecule, viz. the start and the end signatures of the nucleic acid. It is thereby also more specific and accurate than SAGE or MPSS methods in characterizing transcriptomes and defining gene structure by mapping the GIS tags to genome sequences.

Accordingly, the invention provides an isolated oligonucleotide comprising at least one ditag, wherein the ditag comprises two joined first and second sequence tags, wherein the first tag comprises the 5'-terminus sequence and the second tag comprises the 3'-terminus sequence of a nucleic acid molecule or fragment thereof.

Figure 1:
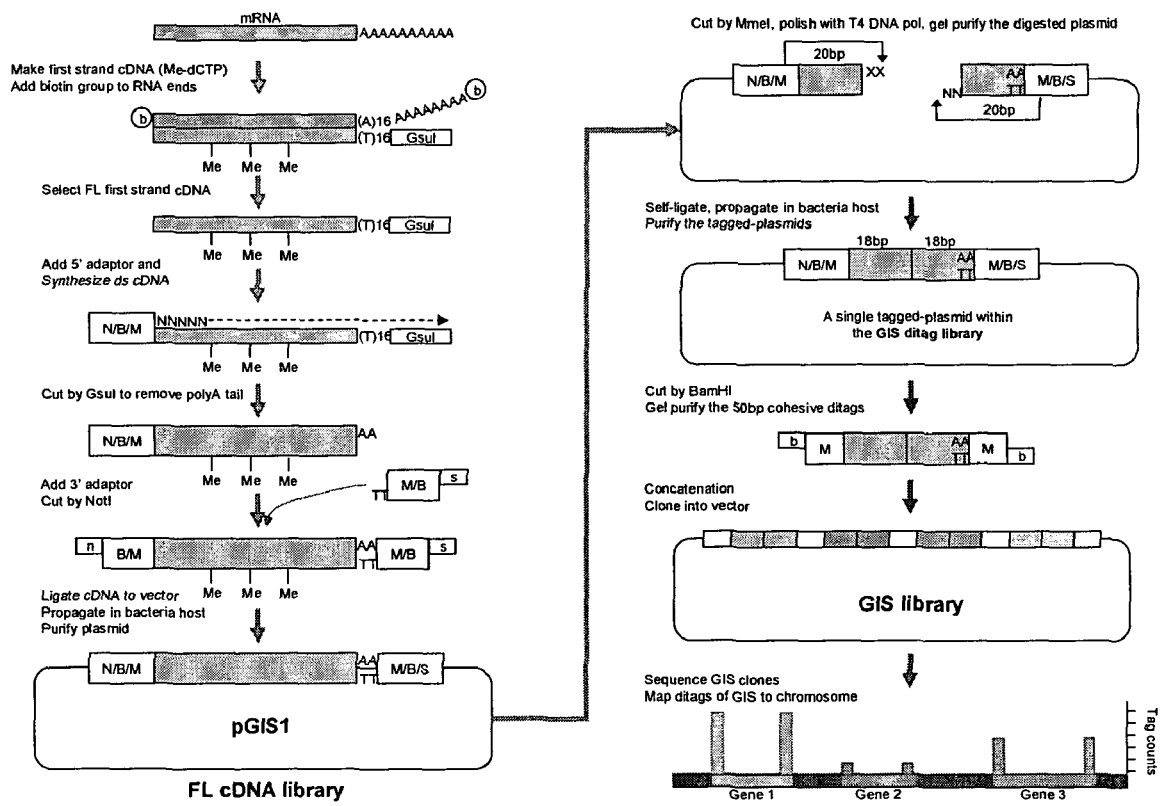
FIG. 1 shows the GIS analysis experimental workflow (bacterial transformation approach). In the figure, the letters N, B, M, S either in capital or small letters denotes the recognition sites for the restriction enzymes Not I, Bam HI, Mme I and Sal I, respectively. The text "Me" represents methylation of the newly-synthesized first-strand cDNA. The polyA sequence depicted corresponds to SEQ ID NO: 26.
Figure 2:
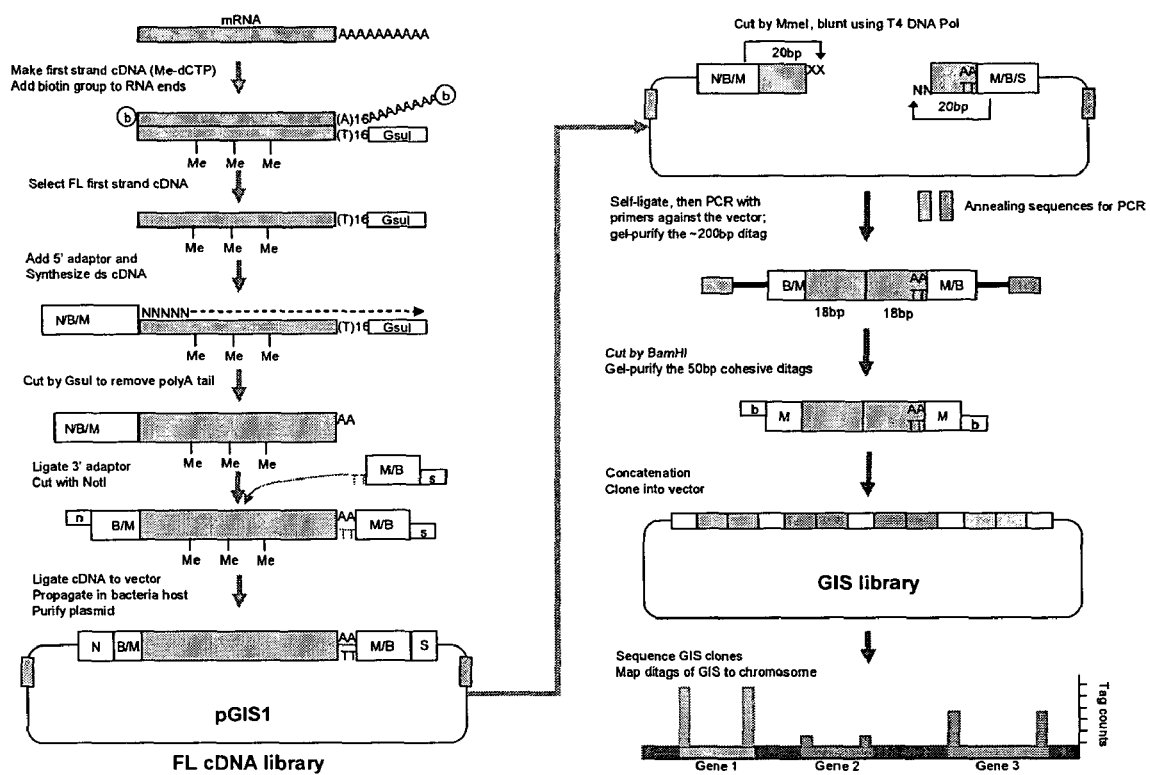
FIG. 2 shows the GIS analysis experimental workflow (PCR-based approach). In the figure, the letters N, B, M, S either in capital or small letters denotes the recognition sites for the restriction enzymes Not I, Bam HI, Mme I and Sal I, respectively. The text "Me" represents methylation of the newly-synthesized first-strand cDNA. The polyA sequence depicted corresponds to SEQ ID NO: 26.

The oligonucleotide of the invention may further comprise two adapters flanking the ditag, wherein each adapter comprises at least one restriction site (see FIG. 1 and FIG. 2). In particular, each adapter comprises at least: a first restriction site which is an asymmetric restriction site and at least a second adjacent restriction site. Therefore, the number of restriction sites present in each adapter may be two or more. Examples of asymmetric restriction sites are homing endonuclease asymmetric recognition sites, and type II (or class II) recognition sites. A list of possible asymmetric restriction sites and corresponding restriction enzymes recognizing such asymmetric sites is reported below. Example of second and further restriction sites may be for example BamHI. This second restriction site is for the purpose of subsequent isolation of a pool of ditags that can then be ligated together to form concatemers.

The original nucleic acid molecule that one intends to reduce (to shrink) may be any natural, any modified or any synthetic nucleic acid molecule. It can also be of any size. The nucleic acid molecule can be a gene (the full-length of a gene) or a fragment thereof. The nucleic acid may be RNA, mRNA, genomic DNA, full-length cDNA, or cDNA or a fragment thereof.

The ditag can also be fully chemically synthesized by comprising the 5' end and 3' end of a nucleic acid molecule which the ditag intends to represent.

The molecule that one intends to reduce may also be a portion or fragment inside a nucleic acid molecule. Accordingly, it is possible to use restriction enzymes recognizing restrictions sites flanking the region which is intended to be reduced. The desired restriction sites may be placed into the appropriate position during the preparation of the nucleic acid molecule, for example a cDNA or full-length cDNA.

According to a particular aspect, the nucleic acid desired to be reduced is a full-length cDNA. Full-length cDNA can be prepared according to any method known in the art. See for example, the cap-trapper approach, for example Carninci et al., 1996, Genomics, Vol.37, 327-336; U.S. Pat. No. 6,143, 528; Edery et al., 1995, Mol. Cell. Biol., Vol.15, No.6, 3363-3371.

Those of skill in the art will know other capture systems, for example, those based on biotin/streptavidin, digoxigenin/anti-digoxigenin for isolation of the full-length cDNAs can be used.

The ditag can be prepared according to any technique known in the art. For example, the original nucleic acid molecule may be cut through any chemical reaction and the obtained 5' and 3' termini ligated to create the ditag.

The nucleic acid molecule which is intended to be reduced, which is preferably prepared comprising two adapters flanking the molecule, may be inserted into a vector. In a particular realisation, each adapter comprises at least one restriction site, preferably comprises at least a first restriction site comprising an asymmetric restriction site and a second restriction site. Accordingly, in the vector used, it is important that the backbone of the vector does not comprise the restriction site or sites present in the adapters.

Accordingly, a library of nucleic acid molecule (for example, a library of full-length cDNAs) is prepared.

Preferably, the nucleic acid molecule is spliced into a ditag or oligonucleotide comprising a ditag by using restriction enzymes which recognize restriction sites flanking the nucleic acid molecule to be reduced. Accordingly, the recognition sites are placed upstream of the 5' terminus and downstream of the 3' terminus of the nucleic acid molecule or fragment thereof desired to be reduced (preferably into the adapters). Accordingly, the oligonucleotide obtained by splicing comprises two adapters flanking the ditag. Each adapter comprising at least one restriction site. Preferably, comprising at least one first restriction site which is an asymmetric site (for example a type II restriction site, like MmeI) and at least a second restriction site (any known restriction site may be used, for example BamHI.

The 5' tag and 3' tag forming the ditag may have the same or different size. Preferably, they have the same number of nucleotides.

The ditag can be of any size, but needs to be meaningful and advantageous over the size of the parental sequence from which it is derived. The preferred size of a tag or ditag is determined by genome complexity. For a bacterial genome a tag from about 8 bp to about 16 bp may be sufficient whereas for a complex genome like the human genome, a 16-20 bp tag (or in other words a 32-40 bp ditag) may be considered. In general, the size of the ditag is from about 12-60 bp.

For the purpose of the present application, the terms 5'-terminus, 5'-end and 5'-tag are equivalent to each other and can be used interchangeably. In the same way, the terms 3'-terminus, 3'-end and 3'-tag are equivalent to each other and can be used interchangeably. In an original nucleic acid molecule or portion inside a nucleic acid molecule that one intends to reduce or represent, each of the 5'-end and 3'-end represents a region or portion most closer to the extremity and most far from the middle region of the molecule.

According to one aspect, the 5'-tag and 3'-tag comprised in the ditag are the regions of the molecule cleaved by a restriction enzyme most closer to the 5'-end and 3'-end, respectively, of the nucleic acid molecule or portion thereof which is intended to be reduced or represented. Accordingly, the size of the ditag can be determined by the restriction enzyme or enzymes used. The invention, therefore, relates to an oligonucleotide comprising at least one ditag, wherein the ditag is obtained by splicing the 5' terminus and the 3' terminus of the nucleic acid molecule in the presence of at least one restriction enzyme, which recognizes the restriction sizes flanking the nucleic acid molecule. Accordingly, the size of the sequence tags is determined by the restriction enzyme used.

When preparing the nucleic acid molecule, for example a full-length cDNA, desired restriction sites flanking the 5'-end and 3'-end of the region which is intended to be reduced or represented are inserted. An example of construction of a full-length cDNA by insertion of desired restriction sites flanking the 5'-end and 3-end is shown in FIG. 1 and FIG. 2. A full-length cDNA library is then prepared, following which a GIS ditag library is subsequently prepared.

As an example, a restriction enzyme recognizing an asymmetric restriction site can be used for the purpose of the preparation of the ditag according to the invention. In particular a type II enzyme, for example MmeI.

As an example, asymmetric sites can be introduced. Asymmetric site sequences useful for the purpose of the present invention are: i) two homing endonuclease asymmetric recognition site sequences or ii) restriction endonuclease asymmetric cleavage sites sequences recognizable by type II restriction enzymes.

Homing endonucleases are sold and described by New England Biolabs, Inc.; a description of the asymmetric site sequences is also available in the New England Biolabs Catalog. These homing endonuclease asymmetric recognition site sequences are from 18 to 39 bp. However, in the present invention the recognition site sequences are not limited to those sequences nor to these sizes. Preferably, the restriction homing endonucleases capable of cutting the asymmetric site sequences are selected from the group consisting of: I-CeuI, PI-SceI, PI-PspI and I-SceI. The list mentioned above however is not exhaustive. Other homing endonucleases known in the art and those which may be later discovered are included in the scope of the present invention.

Examples of type II restriction enzymes include AarI, AcelII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (the list in the web site of Rebase Enzymes®: rebase.neb-.com/cqi-bin/outsidelist; see also Szybalski, W., 1985, Gene, 40:169). The list mentioned above however is not exhaustive. Other type II enzymes known in the art and those which may be later discovered are included in the scope of the present invention.

Examples of recognition sites and cleavage sites of several class II restriction enzymes are (into parenthesis are the recognition site and the cleavage site): BbvI (GCAGC 8/12), HgaI (GACGC 5/10), BsmFI (GGGAC 10/14) SfaNI (GCATC 5/9), and Bsp I (ACCTGC 4/8).

The ditag of the invention can conveniently be ligated or joined in order to form concatemers of ditag. Accordingly, the invention relates to an oligonucleotide comprising 1 to 1000 ditags, in particular 1 to 200, more in particular 8 to 20 ditags. When ditags are concatemerized, a higher yield of information is achieved because the oligonucleotide, vector or clone comprises more ditags. Hence, the concatenation of ditags allows an efficient analysis of the nucleic acid molecules, like full-length cDNAs, in a serial manner by sequencing multiple ditags within a single vector or clone.

The oligonucleotide, ditag or concatemers of ditags can be inserted into a vector either before or after concatemerization.

According to one aspect, the oligonucleotide comprising the ditag is amplified. For example, by using PCR or any other known amplification methods. Accordingly, suitable PCR primers corresponding to specific regions inside the vector are used. Such regions flank the oligonucleotide comprising the ditag and adapters. PCR can be performed directly on the ligation (self-circularization) reaction to obtain short (for example 200 bp) PCR products (see the PCR approach in FIG. 2). These PCR products that contain the required GIS ditags will then be cut with an enzyme recognizing the at least second restriction site (inside the adapters) to generate the required short cohesive ditags. As restriction enzyme recognizing the second or further restriction site, BamHI can for example be used, and cohesive ditags of 50 bp are generated. The advantage of this amplification step is that of generating GIS ditags circumventing the need to produce a GIS ditag library amplification, which can be avoided by not transforming the self-circularized tagged plasmids. The amplified oligonucleotide can then subsequently be excised from the vector (in this example, by digestion with BamHI) and concatenated in long stretches of DNA or RNA for subsequent cloning and sequencing analysis (see FIG. 1 and FIG. 2).

As a particular aspect, the invention discloses a cDNA library wherein the oligonucleotide comprises at least one ditag, and wherein the ditag comprises 34-38 nucleotides and is obtained by splicing nucleotides from the 5' terminus and nucleotides from the 3' terminus of a full-length cDNA or fragment thereof.

The ditag library according to the invention is representative of the library comprising the original nucleic acid molecules. For example, when the library comprising the nucleic acid molecules is a full-length cDNA library, the ditag library is representative of the full-length ditag library Each ditag clone comprises sufficient information characterizing the specific full-length clone. More important, the ditag of the invention comprises the 5'-end and 3'-end of the original full-length cDNA. Hence, the ditag is representative of the structure of the full-length cDNA.

Accordingly, it is sufficient to sequence and analyze the ditag clones of the ditag library. In case a ditag of interest is found, the corresponding full-length cDNA can be selected and prepared from the full-length cDNA library, for example by PCR or directly from target RNA samples by RT-PCR.

The invention provides a method for the preparation of at least one oligonucleotide comprising at least one ditag comprising:
producing at least one nucleic acid molecule;
isolating the 5' terminus and the 3' terminus of the nucleic acid molecule or fragment thereof;
linking the 5' terminus and 3' terminus to create the at least one ditag.

In particular, the invention provides a method for preparing at least one oligonucleotide comprising at least one ditag comprising:
producing at least one nucleic acid molecule flanked by two adapters;
isolating the 5' terminus and the 3' terminus of the nucleic acid molecule; and
linking the 5' terminus and 3' terminus to create the at least one oligonucleotide comprising at least one ditag flanked by the two adapters.

The method further comprising including the oligonucleotide comprising the at least one ditag flanked by the adapters into a vector.

The nucleic acid molecule which is intended to shrink or represent may be RNA, mRNA, genomic DNA, full-length cDNA, or cDNA.

The nucleic acid molecule may be the full-length sequence of a gene or a fragment thereof.

The method of the invention may further comprise the step of determining the nucleotide sequence of the at least one ditag to detect gene expression.

The method may further comprise the steps of: determining the sequence of the at least one ditag; and comparing the ditag nucleotide sequence to a database comprising genomic sequences whereby matching 5' and 3' termini sequences are identified.

More in particular, the invention relates to a method comprising:
producing at least one nucleic acid molecule, for example a full-length cDNA, flanked by two adapters, wherein each adapter comprises at least one restriction;
splicing the 5' terminus and the 3' terminus of the nucleic acid molecule or fragment thereof to produce at least one ditag by adding at least one restriction enzyme recognizing the recognition sites.

Any recognition site known in the art may be used. Restriction enzyme recognizing at least one recognition site within the nucleic acid molecule and which can be used will be evident to those skilled in the art (see for example, Current Protocols in Molecular Biology, Vol. 2, 1995, Ed. Ausubel, et al., Greene Publish. Assoc. & Wiley Interscience, Unit 3.1.15; New England Biolabs Catalog, 1995).

For example, the two recognition sites may be asymmetric recognition sites:

The asymmetric recognition site are: i) homing endonuclease asymmetric recognition site sequences or ii) restriction endonuclease asymmetric cleavage sites sequences recognizable by type II restriction enzymes.

The type II restriction enzyme is selected from the group consisting of AarI, AceIII, AloI, BaeI, Bbr7I, BbvI, BbvII, BccI, Bce83I, BceAI, Bcefl, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (see the list in the web site of Rebase Enzymes®: rebase.neb.com/cgi-bin/outsidelist; see also Szybalski, W., 1985, Gene, 40:169; and). The list mentioned above however is not exhaustive. Other type II enzymes known in the art and those which may be later discovered are included in the scope of the present invention.

The enzyme recognizing the homing endonuclease asymmetric restriction site is selected from the group consisting of: I-CeuI, PI-SceI, PI-PspI and I-SceI. The list mentioned above however is not exhaustive. Other homing endonucleases known in the art and those which may be later discovered are included in the scope of the present invention.

A particularly preferred tagging enzyme, according to the invention, is an enzyme which cleaves 20/18 nucleotides 3' of its recognition site forming 3' overhanging ends, such as MmeI Artificial restriction endonucleases can also be used. These endonucleases may be prepared by protein engineering. For example, the endonuclease FokI has been engineered by insertions so that it cleaves one nucleotide further away from its recognition site on both strands of the DNA substrates. See Li and Chandrasegaran, Proc. Nat. Acad. Sciences USA 90:2764-8, 1993. Such techniques can be applied to prepare restriction endonucleases with desirable recognition sequences and desirable distances from recognition site to cleavage site. The method further comprises producing concatemers of ditag. The concatemers may be generally about 1 to 1000 ditags, in particular 1 to 200 ditags, more in particular 8 to 20 ditags. While these are preferred concatemers, it will be apparent that the number of ditags which can be concatenated depends on the length of the individual tags and can be readily determined by those of skilled in the art without undue experimentation. After formation of concatemers, multiple tags may be cloned into a vector for sequence analysis, or ditags or concatemers can be directly sequenced without cloning by methods known to those of skill in the art.

The ditags present in a particular clone can be sequenced by standard methods (see for example, Current Protocols in Molecular Biology, supra, Unit 7) either manually or using automated methods.

As described above, the method comprises introducing the oligonucleotide comprising the at least one ditag in a vector.

With the term vector or recombinant vector it is intended a plasmid, virus or other vehicle known in the art that has been manipulated by insertion or incorporation of the ditag genetic sequences. Such vectors contain a promoter sequence which facilitates the efficient transcription. The vector typically contains an origin of replication, a promoter, as well as specific genes which allow phenotypic selection of the transformed cells. Vectors suitable for use in the present invention include for example, pBlueScript (Stratagene, La Jolla, Calif.); pBC, pZErO-1 (Invitrogen, Carlsbad, Calif.) (see FIG. 8) and pGEM3z (Promega, Madison, Wis.) or modified vectors thereof as well as other similar vectors known to those of skill in the art. As a particular realisation, the pGEM3z vector has been modified, and will be referred to as pGIS1 (see also FIGS. 7 and 10). pGEM vectors have also been disclosed in U.S. Pat. No. 4,766,072, herein incorporated by reference.

For the production of the parental nucleic acid molecule, for example full-length libraries and the GIS ditag libraries, suitable vectors are used. Accordingly, suitable vectors, which are within the scope of the present invention, are those wherein the backbone of the vector does not comprise the same restriction site comprised in the adapters flanking the parental nucleic acid molecule or the ditag, after insertion of the parental nucleic acid molecule. Preferably, the invention provides a vector wherein the vector backbone (other than within the stuffer region that is removed during insertion of the parental nucleic acid molecule) does not comprise the asymmetric restriction site and the second or further restriction site which are comprised into the adapters. In particular, the vector does not comprise the at least asymmetric II restriction site (for example type II restriction site) and the at least second or further restriction site comprised in the adapters. More preferably, the vector backbone (other than within the stuffer region that is removed during insertion of the parental nucleic acid molecule) does not comprise MmeI and BamHI.

Figure 7:
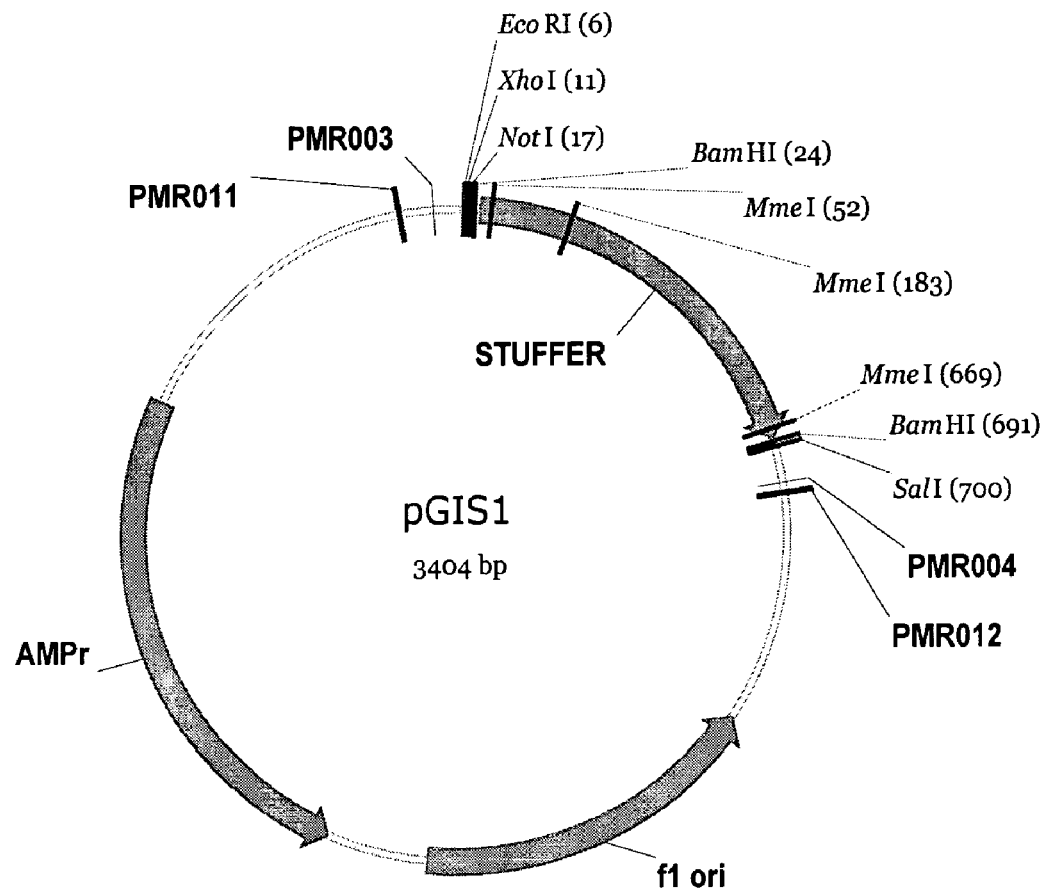
FIG. 7 shows the pGIS1 vector construct.

An example of such a vector not comprising MmeI in any region outside of the stuffer is the vector pGIS1 shown in FIG. 7 and FIG. 10. In pGIS1 the MmeI recognition sites were deleted by mutagenesis. The sequence is shown in FIG. 10 and in SEQ ID NO:18. In FIG. 10, the stuffer region between the sites Not I and Sal I has been highlighted. The invention also related to the pGIS vector comprising the oligonucleotide according to any embodiment of the invention.

The oligonucleotide(s), ditag(s) or concatemer(s) of the invention may also be ligated into a vector for sequencing purposes.

Vectors in which the ditags are cloned can be transferred into a suitable host cell. Host cells are cells in which a vector can be propagated and its DNA expressed. The term also includes any progeny of the subject host cell. It is understood that all progeny may not be identical to the parental cell since there may be mutations that occur during replication. However, such progeny are included when the term host cell is used. Methods of stable transfer, meaning that the foreign DNA is continuously maintained in the host, are known in the art.

Transformation of a host cell with a vector containing ditag(s) may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed by electroporation or other commonly used methods in the art.

An embodiment of this is shown in FIG. 1 and FIG. 2. According to this embodiment, the method of the invention comprises:

producing at least one nucleic acid molecule comprising a full-length cDNA molecule flanked by two adapters; each adapter comprising MmeI recognition sites and another recognition site, which may be BamHI, flanking the 5' terminus and 3' terminus of the full-length cDNA;

splicing the 5' terminus and the 3' terminus of the full-length cDNA to produce at least one ditag, comprising cleaving the full-length cDNA with MmeI which forms 3' overhanging tag ends, and ligating the two 5' and 3' termini tags to produce the ditag.

As shown in FIG. 1 and FIG. 2, the use of restriction enzymes may leave 5' and 3' double stranded end comprising a short overhanging end (also referred to as sticky end or cohesive end) consisting of few nucleotides. In particular, by using MmeI, the produced 5' and 3' ends consist each of a 20 bp double strand and two nucleotides as 3' overhanging ends. The two tags may be followed by blunt-ending and intramolecular self ligation to produce tagged plasmids that contain 18 bp signature sequence as 5' end and another 18 bp signature sequence as 3' end of the parental transcript. However, the number of nucleotides cut by MmeI is variable. Accordingly, the ditag obtained by using MmeI may be of 34-38 bp.

The vector which has been used for the preparation of full-length cDNA library is pGIS1. As mentioned above, pGIS1 does not contain in its backbone MmeI restriction sites, other than within the stuffer region between Not I and Sal I, this stuffer region being subsequently removed during production of the libraries.

The oligonucleotide comprising the ditag flanked by the adapters is cut out form the GIS ditag library and linked to other oligonucleotides comprising ditag and adapters to form concatemers of ditags. The concatemers of ditag are then cloned into a vector for sequencing analysis.

Before cutting the oligonucleotide out from the GIS ditag library, it can be amplified directly from the ligation (self-circularization) reaction mix, for example by PCR using suitable primers. The recovered amplified oligonucleotide comprising ditag and adapters is then linked to other oligonucleotides comprising ditag and adapters to form concatemers of ditags. The concatemers of ditag are then cloned into a vector for sequencing analysis.

The method may further comprise the steps of:
determining the nucleotide sequence of the ditag;
detecting the gene expression;
and/or comparing the determined nucleotide sequence to a database comprising genomic sequences whereby matching 5' and 3' termini sequences are identified.

In particular, the at least one ditag comprises 36 nucleotides and the first and second sequence tags comprise each 18 nucleotides.

As mentioned above, the ditag according to the invention includes the "signature" (consisting of the 5' and 3' ends) of the nucleic acid molecule which is intended to be reduced or represented. Such ditags, preferably cDNA ditags, of a library may be concatenated and sequenced. The paired 5' and 3' signature sequences (tags) of a transcript in a ditag delineate the starting and ending points of transcripts. The ditag can be split up in the two tags during data analysis and mapped head-to-head in a specific region within a reasonable distance on a chromosome of an assembled genome sequence. The genomic DNA sequence in between these two tags is the full structural content of the prospective gene, including exons and introns.

Figure 3:
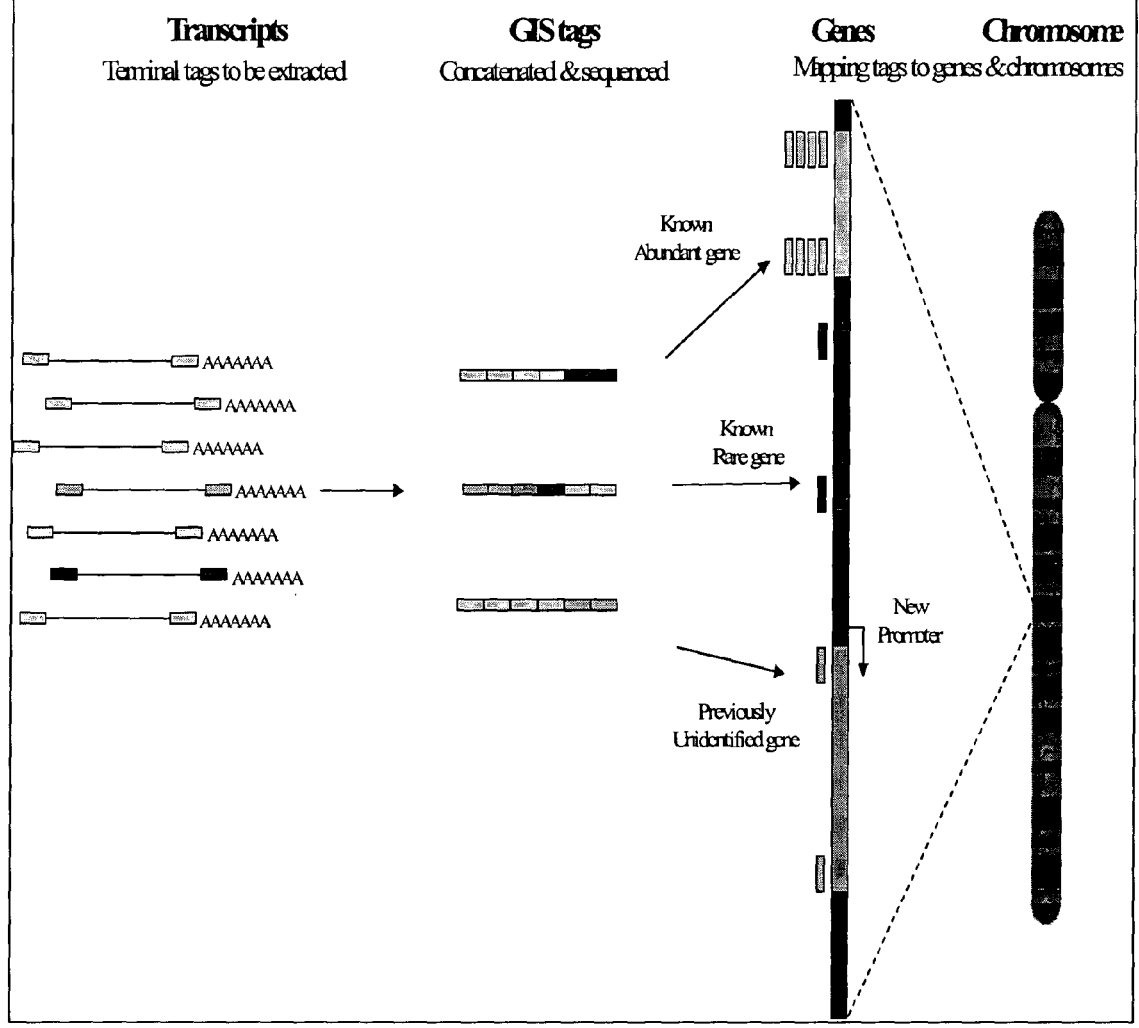
FIG. 3 shows the GIS application of mapping transcriptome to genome.

A general description of genome mapping using the ditag of the invention is shown in FIG. 3.

A modest sequencing run can generate sufficient data to characterize a transcriptome not only by determining the level of transcript abundance but also by defining the structure of transcripts using the revealed 5' and 3' regions. This results in about over 20-fold more efficient than EST sequencing Because the tags of the ditag can be matched to any genome, for example to human genomic sequences, PCR and RT-PCR primers can then be designed based on the matching genomic sequence.

Accordingly, a further aspect of the invention relates to a method for genome mapping, comprising:
preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
mapping each of the two tags of the at least one ditag on the genome; and
defining the structural region of the corresponding gene on the genome map.

Further, it is also an aspect of the invention to provide a method of gene discovery comprising:
preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
comparing the obtained at least one ditag with a genome map and/or a gene database;
detecting matching of the 5' and 3' termini tags on the genome map but detecting no match on one or more of the known gene database;

The method further comprises the step of recovering the full-length nucleic acid molecule corresponding to the newly discovered gene.

The invention also provides a method for recovering full-length cDNA comprising:
preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;
sequencing the obtained oligonucleotide ditag;
determining the ditag of interest; and
recovering the full-length cDNA corresponding to the ditag of interest from the full-length cDNA library.

The invention also provides a method for quantifying the transcriptional activity of a gene comprising:
preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;
sequencing the obtained oligonucleotide ditag;
determining the frequency of the sequenced ditag which corresponds to the transcriptional activity of the gene.

Having now generally described the invention, the same will be more readily understood through reference to the following examples which are provided by way of illustration, and are not intended to be limiting of the present invention.

EXAMPLES

GIS oligonucleotides for cDNA synthesis, the structure of a generic 50 bp cohesive ditag, primers used for the construction of vector pGIS1, and ds-DNA adapter which are used in the examples are listed below.

GIS Analysis Oligos for cDNA Synthesis
GsuI-oligo dT primer:

```
                                              (SEQ ID NO: 1)
5'-GAGCTCCTTCTGGAGTTTTTTTTTTTTTTTVN-3'
```

NotI/BamHI/MmeI(N)6 primer linker (top):

```
5'-AATTCGCGGCCGCTTGGATCCGACNNNNNN   (SEQ ID NO: 2)
```

NotI/BamHI/MmeI(N) primer linker (bottom):

```
5'-p-GTCGGATCCAAGCGGCCGCG-3'        (SEQ ID NO: 3)
```

NotI/BamHI/MmeI(N)5 primer linker (top):

```
5'-AATTCGCGGCCGCTTGGATCCGACGNNNNN   (SEQ ID NO: 4)
```

MmeI/BamHI/SalI adapter (top):

```
    5'-TCGACCCAGGATCCAACTT-3'       (SEQ ID NO: 5)
```

MmeI/BamHI/SalI adapter (bottom):

```
5'-p-GTTGGATCCTGGG- 3'          (SEQ ID NO: 6)

PMR003:
5'-GTAAAACGACGGCCAGT-3'         (SEQ ID NO: 7)

PMR004:
5'-GGAAACAGCTATGACCATG-3'       (SEQ ID NO: 8)

PMR006:
5'-TAATACGACTCACTATAGGG-3'      (SEQ ID NO: 9)

PMR011:
5'-GATGTGCTGCAAGGCGATTAAG-3'    (SEQ ID NO: 10)

PMR012:
5'-AGCGGATAACAATTTCACACAGG-3'.  (SEQ ID NO: 11)
```

Structure of a Generic 50 bp Cohesive Ditag

```
5'-GATCCGACXXXXXXXXXXXXXXXXXXNNNNNNNNNNNNNNNNNNAAGTTG    (SEQ ID NO: 12)

GCTGXXXXXXXXXXXXXXXXXXNNNNNNNNNNNNNNNNNNTTCAACCTAG-5' (SEQ ID NO: 13)
```

Wherein X and N may be any of A, C, G or T.
Primers Used for the Construction of Vector PGIS1

```
Mme_mut1:
5'-p-CGCTCTCCTGTACCGACCCTGCCGCTTAC-3'   (SEQ ID NO: 14)

Mme_mut2:
5'-p-AACTATCGTCTTGAGACCAACCCGGTAAG-3'   (SEQ ID NO: 15)
``` ds-DNA Adapter

```
5'-AATTCTCGAGCGGCCGCGATATCG-3'      (SEQ ID NO: 16)

3'-GAGCTCGCCGGCGCTATAGCTTAA-p-5'    (SEQ ID NO: 17)
``` pGIS1 Sequence

The sequence of pGIS1 (SEQ ID NO:18) is shown in FIG. 10.

Example 1

The Method

The experimental procedure of GIS ditag analysis has been carried out according to the following modules of cDNA library construction and analysis:
(1) The full-length cDNA library which introduces the MmeI sites flanking both ends of each cDNA insert;
(2) The GIS ditag library in which each clone contains a 5' 18 bp signature and a 3' 18 bp signature of a transcriptional unit;
(3) The GIS library for clones of concatenated GIS ditags;
(4) GIS sequencing analysis.

1. GIS Full-length cDNA Library with Addition of MmeI Sites for Each cDNA Inserts The outline of procedure of this section was as follows: starting from high quality mRNA, the first cDNA was synthesized with a GsuI-oligo dT primer (SEQ ID NO:1).

The first strand cDNA/RNA hybrids was subjected to a full-length enrichment procedure by the biotinylation-based cap-trapper approach. Any cap-trapper approach known in the art can be used, for example Carninci et al., 1996, Genomics, Vol.37, 327-336; U.S. Pat. No. 6,143,528; Edery et al., 1995, Mol. Cell. Biol., Vol.15, No.6, 3363-3371).

The enriched full-length first strand cDNA was the template for second cDNA synthesis primed with adapter-primer (NotI/BamHI/MmeI-(N)5 and -(N)6, (SEQ ID NOS: 2-4) that contain a MmeI, a BamHI, and a NotI site.

After the double strand cDNA was made, the cDNA poly-A/T tail was cleaved off by GsuI restriction enzyme. GsuI is another Type-II endonuclease that cleaves DNA 16 bp from its recognition site. At the GsuI cleavage end, an adapter containing a MmeI, a BamHI site, and a SalI cohesive end was ligated to the cDNA (SEQ ID NOS: 5-7).

Following a NotI digestion, the full-length cDNA was inserted into the vector pGIS1, between the NotI and SalI sites in the polylinker. The vector pGIS1 (see FIGS. 7 and 10) is modified from pGEM3z (Promega).

1-1. mRNA Preparation

The total mRNA has been prepared from mouse embyonic stem cell line E14 using Trizol reagent (Invitrogen). However, any standard method (as those described in Sambrook J. and Russell D. W., 2001, Molecular Cloning, Cold Spring Harbor Laboratory Press) may also be used.

mRNA (polyA RNA) was purified by oligo dT magnetic beads according to standard techniques (for example, Sambrook and Russell, 2001, as above). Alternatively, purification may be carried out by affinity column according to standard techniques (for example, Sambrook and Russell, 2001, as above).

1-2. First Strand cDNA Synthesis and Full-length Selection

In this step, the first cDNA is synthesized with a GsuI-oligo dT primer. Then, the first strand cDNA/RNA hybrids are subjected to a full-length enrichment procedure by the biotinylation-based cap-trapper approach.

GsuI-oligo dT primer:

```
                                            (SEQ ID NO: 1)
5'-GAGCTCCTTCTGGAGTTTTTTTTTTTTTTTTVN-3'
```

The following were mixed:

| | |
|---|---|
| GsuI-oligo dT primer (7 μg/μl) | 2 μl |
| PolyA RNA (20 μg) | 18 μl |

The obtained solution was heated to 65° C. for 10 min and 37° C. for 1 min.

Then, spin tube in microfuge and the following substances were added:

| | |
|---|---|
| 2× GC-I buffer (Takara) | 75 μl |
| RNase inhibitor Promega) | 1 μl |
| 10 mM dNTP (with methyl-dCTP) | 4 μl |
| Saturated trehalose | 10 μl |
| 4.9M sorbitol | 26 μl |
| Superscript II reverse transcriptase (Invitrogen) | 15 ul |

The obtained solution was incubated at 37° C. for 10 min, 42° C. for 30 min 50° C. for 20 min and 55° C. for 20 min. 2

µl of proteinase K (20 mg/ml) were added. The obtained solution was Incubated at 45° C. for 15 min followed by phenol/chloroform extraction and isopropanol precipitation (according to standard technique, eg. Sambrook and Russel, 2001, as above).

The RNA/cDNA heteroduplex was re-suspended into 44.5 µl of ddH$_2$O. 3 µl of 1.1 M NaOAc pH 4.5 and 2.5 µl of 100 mM NaIO$_4$ were added to oxidize the diol structures of the mRNA. 50 µl of the reaction solution were incubated on ice in the dark for 45 min followed by adding 0.5 µl of 10% SDS, 11 µl of 5 M NaCl and 61 µL of isopropanol to precipitate the RNA/DNA. The precipitated RNA/DNA was resuspended in 50 µl of ddH$_2$O. 5 µL 1M NaOAc (pH6.1), 5 µL 10% (w/v) SDS and 150 µL 10 mM long-arm biotin hydrazide were added to biotinylate the RNA. The reaction was incubated at room temperature in dark overnight. The biotinylated RNA/DNA was precipitated by adding 5 µL 5M NaCl, 75 µL 1M RNase-free NaOAc (pH6.1), and 750 µL 100% EtOH or 200 µL of 100% Isopropanol. Incubate at −80° C. for 30 min by spin 14 krpm at 4° C. for 30 min.

The pellet was washed w/70% (v/v) EtOH/30%, DEPC-treated ddH$_2$O (DEPC is diethylpyrocarbonate, which is an RNase inhibitor), and 14 krpm spin was carried out at 4° C. for 10 min. The extra liquid was carefully removed. Then, the pellet was air-dried, and resuspended in 400 µL DEPC-ddH$_2$O. Then 50 µL 10×RNaseI buffer and 25 units RNaseI/µg of starting mRNA were added. The obtained solution was incubated at 37° C. for 30 min. 10 µL of 10 mg/mL Yeast tRNA (Ambion) and 150 µL of 5M NaCl were added to stop the reaction.

While biotinylating the RNA-DNA heteroduplex, the Streptavidin Dynabeads were prepared as follows: 400 µL of M-280 Streptavidin beads (Dynal) were pipetted into an RNase-free Eppendorf tube, the beads placed on a magnet, left staying for at least 30 min, and then the supernatant was removed. The beads were re-suspended in 400 µL 1× binding buffer (2M NaCl, 50 mM EDTA, pH 8.0). The tube was placed on a magnet, waited at least 30 min, and then the supernatant was removed. The 1× binding buffer wash was repeated for 2 more times. The beads were re-suspended in 400 µL 1× binding buffer with 100% g of Yeast tRNA, and then incubated at 4° C. for 30 min with occasional mixing. The tube was placed on a magnet stand, waited at least 30 seconds, and the supernatant was removed. The beads were washed with 1× binding buffer for 3 times. The beads and RNA/DNA heteroduplex were mixed (the total volume now was 660 µL, and the binding condition was at 1 M NaCl). The mixture was rotated at room temperature for 30 min.

The tube was placed on a magnet stand, waited at least 30 seconds, and the supernatant removed (the supernatant was saved as "unbound").

The beads were washed two times with 400 µL of 1× binding buffer. Washed with 400 µL of 0.4%(w/v) SDS plus 50 µg/mL Yeast tRNA. Washed with 400 µL of 1× wash buffer (10 mM Tris-HCl pH7.5, 0.2 mM EDTA, 10 mM NaCl & 20%(v/v) glycerol, 40 µg/mL Yeast tRNA). And washed w/400 µL of 50 µg/mL Yeast tRNA. For all washes the tube was placed on a magnet stand, waited for at least 30 seconds, and the supernatant was removed.

The first strand cDNA was released by alkali hydrolysis of RNA. The following was added: 50 µL 50 mM NaOH and 5 mM EDTA (pH8.0). The tube was rotated at 65° C. for 10 min. The tube was placed on a magnet stand, and the supernatant transferred to another tube containing 50 µL 1M Tris-Cl (pH7.5).

The lysis procedure was repeated for 2 more times. The final volume of supernatant was 300 µL (containing the first strand cDNA).

The cDNA was extracted by phenol/chloroform extraction and precipitate by 1 mL ethanol with glycogen. The cDNA was re-suspended in 5 µL LoTE (0.1×) LoTE is low salt Tris-EDTA buffer (3 mM Tris-HCl pH 7.5 and 0.2 mM EDTA pH7.5)).

1-3. Second Strand cDNA Synthesis

The following reagents were added to the each corresponding tube on ice.

| | |
|---|---|
| cDNA in LoTE | 5 µL |
| Linker (N5) | 1.6 µg |
| Linker (N6) | 0.4 µg |
| Soln II (Takara ligation kit) | 10 µL |
| Soln I (Takara ligation kit) | 20 µL |

Linker (N6) is:
NotI/BamHI/MmeI(N)6 primer linker (top):

(SEQ ID NO: 2)
5'-AATTCGCGGCCGCTTGGATCCGACNNNNNN

NotI/BamHI/MmeI(N) primer linker (bottom):

(SEQ ID NO: 3)
5'-p-GTCGGATCCAAGCGGCCGCG-3'

Linker (N5) is:
NotI/BamHI/MmeI(N)$_5$ primer linker (top):

(SEQ ID NO: 4)
5'-AATTCGCGGCCGCTTGGATCCGACGNNNNN

NotI/BamHI/MmeI(N) primer linker (bottom): is the sequence (SEQ ID NO:3) indicated above.

The cDNA and linker mixture was incubated at 16° C. overnight. And the following were added:

| | |
|---|---|
| ddH$_2$0 | 20 µL |
| 10× ExTaq buffer (Takara) | 8 µL |
| 2.5 mM dNTP | 8 µL |
| ExTaq polymerase (Takara) | 4 µL |

The mixture was preheated in a thermo-cycler 65° C., 5 min→68° C., 30 min→72° C., 10 min., followed by phenol/chloroform extraction and ethanol ppt with glycogen, and re-suspended in 85 µl ddH$_2$O.

1-4. Removal of PolyA Tail by GsuI Digestion

The following reagents were added to the tube.

| | |
|---|---|
| cDNA | 85 µL |
| GsuI (Fermentas) | 5 µL |
| 10× bufferB (Fermentas) | 10 µL |

The mixture was incubated at 30° C. for 2 hours, followed by phenol/chloroform and ethanol precipitation. The pellet was re-suspended in 10 ul ddH$_2$O, and the following 3' adaptor ligation reaction was carried out.

1-5. Addition of 3' adapter with MmeI and BamHI and SalI sites. The following components were added to the tube containing 10 µl of sample. The 10 µl of sample was the double-stranded full length cDNA which has had the poly(A) tail removed by GsuI digestion.

| 5× ligation buffer | 10 µL |
| --- | --- |
| GsuI SalI adapter (0.4 µg/µL) | 25 µL |

[The GsuI SalI adapter is MmeI/BamHI/SalI adapter)

| T4 DNA ligase (5 units/ul) (Invitrogen) | 5 µL |
| --- | --- |

MmeI/BamHI/SalI adapter (top):

(SEQ ID NO: 5)
5'-TCGACCCAGGATCCAACTT-3'

MmeI/BamHI/SalI adapter (bottom):

(SEQ ID NO: 6)
5'-p-GTTGGATCCTGGG-3'

The reaction was incubated at 16° C. overnight, followed by phenol/chloroform extraction and ethanol precipitation, and the pellet re-suspended in 41 µl dH$_2$O.

1-6. NotI Digestion and cDNA Size Fractionation

The following were added on ice and in order:

| NEB Buffer 3 | 5 µL |
| --- | --- |
| NotI (10 units/µl) (NEB) | 4 µL |

The obtained solution was incubated at 37° C. for 1-2 hours.

cDNA Size Fractionation Columns were prepared (the Invitrogen instructions were followed: uncap the column (bottom first) and allow it to drain completely; wash 5 times with 800 µL $T_{10}E_{0.1}N_{25}$ Buffer, allowing the column to drain completely each time). The DNA sample was loaded onto the column. The flow-through was collected in an Eppendorf tube (fraction 1). 100 µL of $T_{10}E_{0.1}N_{25}$ Buffer were added. The flow-through was collected in an Eppendorf tube (fraction 2). Another 100 µL of $T_{10}E_{0.1}N_{25}$ Buffer was added. The flow-through collected, one drop per pre-numbered Eppendorf tube (beginning with fraction 3, each drop was about 30-40 µL).

Whenever the column runs dry, another 100 µL of $T_{10}E_{0.1}N_{25}$ Buffer may be added.

Up to drop 20 should be collected (according to the Invitrogen protocol). 3 µL of each fraction were run on agarose gel to visualize the cDNA size in each fraction. Pool fractions were showing cDNA≧1.0 kbp (usually up to 2-3 kbp). Pooled samples were kept neat (using a cuvette soaked at least 30' in slightly acidified 100% EtOH, rinsed 5 times with ddH$_2$O, and saving sample. This is what has to be ligated).

If only one fraction is to be used, precipitate it and use the half to all of it, depending on what the gel looks like.

At this point the cDNA fragments have the NotI cohesive end at 5' side and SalI cohesive end at 3' side, and are ready to be cloned in vector.

1-7. Ligation of cDNA with Linearized Plasmid pGIS1.

Figure 9:
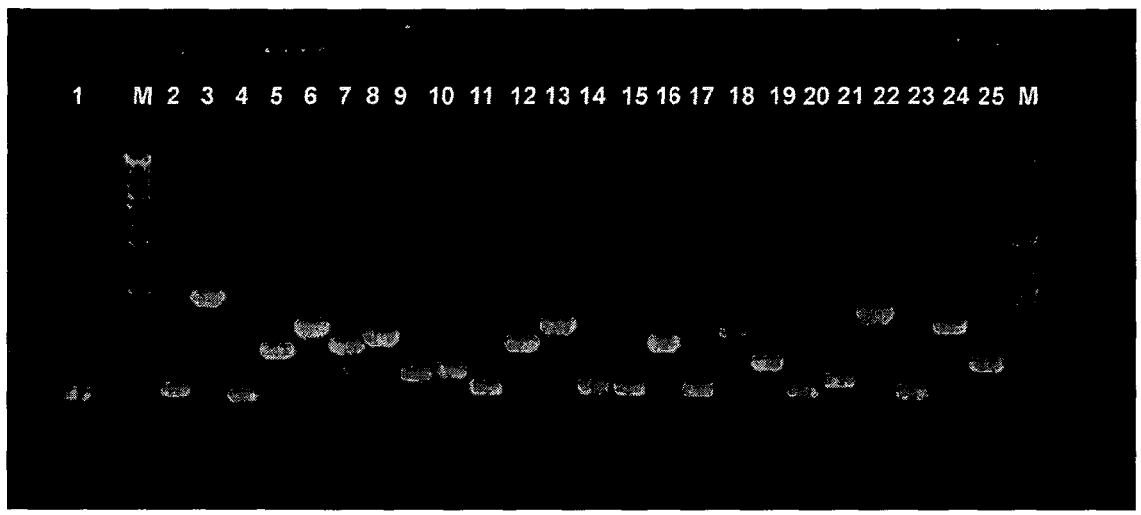
FIG. 9 shows a typical example of the QC (quality check) performed on multiple clones from the GIS library using PCR. Lane 1: pZErO-1 vector as negative control. M: 1 kb+DNA ladder. Lanes 2-25: randomly-picked clones.

1-7-1 The cloning vector pGIS1 was prepared by NotI and SalI digestion. The vector sequence of pGIS1 is shown in FIGS. 7 and 9.

pGIS1 Cloning Vector Construction (I) Site-Specific Mutagenesis of pGEM3z to Create MmeI-minus Vector The vector pGIS-1 was derived from pGEM3z (Promega). pGEM3z originally contained two MmeI recognition sites that were knocked-out by site-directed mutagenesis. The QuikChange Multi kit (Stratagene) was used, together with mutagenic primers:

Mme_mut1:

(SEQ ID NO: 14)
5'-p-CGCTCTCCTGTA<u>CCGAC</u>CCTGCCGCTTAC-3'

Mme_mut2:

(SEQ ID NO: 15)
5'-p-AACTATCgTCTTgAg<u>ACCAA</u>CCCggTAAg-3'

(II) Modification of Polylinker Region

The polylinker region was modified by simple insertion of a ds-DNA adapter at the existing EcoRI site. Additional recognition sites thus introduced are: XhoI, NotI and EcoRV (EcoRV is deleted upon insertion of the stuffer fragment (see below)).

ds-DNA adapter:

(SEQ ID NO: 16)
5'-AATTCTCGAGCGGCCGCGATATCG-3'

(SEQ ID NO: 17)
3'-GAGCTCGCCGGCGCTATAGCTTAA-p-5'

(III) Stuffer Fragment Insertion

An approximately 690 bp fragment was inserted between the NotI and SalI sites of the modified vector (see vector sequence in FIG. 10). This facilitated the production of NotI/SalI double-digested vector, as the stuffer can be clearly visualized and excised during gel-purification.

The linearized plasmid was gel purified.

1-7-2 The cDNA was ligated to the pGIS1 vector overnight and the constructs were transferred into electrocompetent *E. coli* TOP 10 cells by electroporation according to standard techniques (see Sambrook and Russel, 2001, as above).

1-8. Library QC (QC=Quality Check)

A dilution series of 1-100 µL of transformants was plated out onto LB agar plates with antibiotic selection. The colonies were incubated overnight and counted to determine the library titer.

Between 24 to 96 colonies (arbitrary numbers) were picked and the inserts size determined by direct colony PCR and agarose gel electrophoresis (according to standard techniques, eg. Sambrook and Russel, 2001, see above). The percentage of cDNA insert and the average insert size were estimated.

At this stage, the GIS full-length cDNA library may be stored as ligation reactions or as transformants in *E. coli* cells, according to standard methodology (Sambrook and Russel, 2001, see above).

Example 2

2. GIS Ditag Library

The cDNA clones made from steps 1-1 to 1-8 contained a MmeI site (TCCGAC) at the 5' side and another MmeI site (TCCAAC) in reverse orientation at the 3' end. Note that these two MmeI recognition sites are two isoforms that can be recognized by MmeI (TCCRAC 20/18, where R=(A/G)). The sequence difference here will be useful later for directional indication. MmeI restriction enzyme will cleave these clones 20 bp into the cDNA fragments from their 5' and 3' ends. Consequently, despite the variable sizes of the digested cDNA, the vector plus the 20 bp cDNA signature tags on each end of all clones will be of a constant size that can be easily recognized upon agarose gel electrophoresis, and can be easily purified from the unwanted cDNA fragments.

The gel-purified vector plus tags can then be self-ligated to give a "tagged plasmid" containing the 5' and 3' GIS signature tags.

2-1. Plasmid Preparation

The GIS full-length cDNA library was amplified once by plating an appropriate number of clones on large (22×22 cm) agar plates (Genetix). The number of colonies required was determined by the estimated transcriptome size. After an overnight 37 C incubation, the resultant bacterial colonies were harvested and pelleted by centrifugation at 3000 g for 30 min. Plasmid DNA preparation was performed using the Qiagen HiSpeed Plasmid Maxi kit. The quality of the DNA obtained was examined by agarose gel electrophoresis and restriction digestion. Approximately 300,000 colonies can be processed to yield at least 1 mg of plasmid DNA.

2-2. MmeI Digestion

Approximately 10 g of plasmid DNA was digested using MmeI as per manufacturer's conditions (NEB), ensuring that the number of units of enzyme used was always less than 4-fold excess to prevent methylation-induced inhibition. Digestion proceeded at 37 C for 2-6 hrs.

Figure 4:
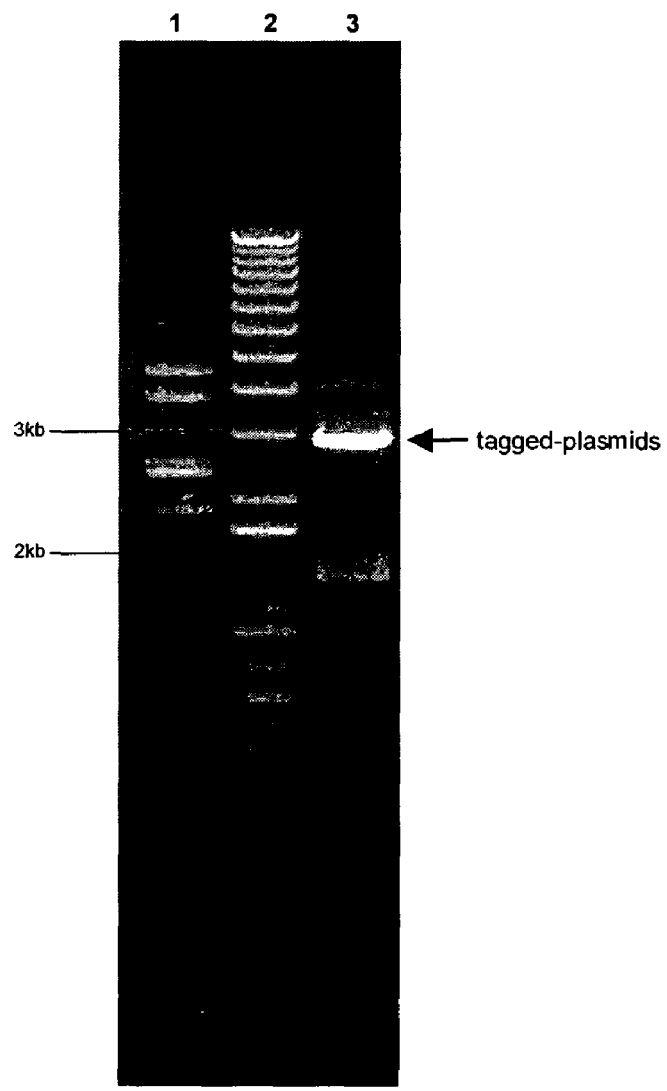
FIG. 4 is an electrophoresis gel showing MmeI digestion of a mix of original full-length cDNA clones. Lane 1: original supercoiled plasmid preparation. Lane 2: 1 kb DNA ladder. Lane 3: MmeI digestion products. The arrowhead shows the position of all the linearized tagged-plasmids.

An aliquot of the digestion reaction was examined on an agarose gel: a strong band of approximately 2800 bp in size corresponding to the linearized vector containing the GIS signature tags were easily observed, together with a number of fragments derived from the excision of cDNA from the original plasmids (see FIG. 4).

2-3. Linear Vector-GIS Ditag Purification

The digestion reaction was electrophoresed on 0.7% agarose, and the 2800 bp vector-GIS tag band was excised and purified using the Qiagen agarose gel extraction kit.

2-4. Vector-GIS Ditag Self Ligation to Create "Tagged-Plasmids"

MmeI digestion resulted in a 2 bp overhang on both the 5' and 3' signature tags. These were removed (polished off) using T4 DNA polymerase (Promega), leaving behind 18 bp tags:

| | |
|---|---|
| (0.5-2.0 ug) DNA | 50 μL |
| 10× Y+/TANGO buffer (Fermentas) | 6.0 μL |
| 0.1M DTT | 0.3 μL |
| T4 DNA polymerase | 5 units/μg |
| 10 mM dNTP | 0.6 μL |
| ddH₂O | to 60.0 μL |

Incubated at 37 C, for 5 min, then inactivate at 75 C for 10 min

The purified, blunted DNA was then ethanol precipitated and resuspended at a concentration of approximately 20 ng/μl. Self-ligation (intramolecular recircularization) was carried out as follows:

| | |
|---|---|
| Approx. 350 ng DNA | 15.0 μL |
| Ligation Solution I (Takara Ligation Kit 2) | 15.0 μL |
| Incubated at 16 C., 2 hr to overnight | |
| 2-5. Creation of Di-signature Tags (ditags) | |

The goal of this step was to obtain the GIS di-signature tags in a form quantitatively representative of the original cDNA library from which the tagged-plasmids were derived.

Structure of a Generic 50 bp Cohesive Ditag

```
                                            (SEQ ID NO: 12)
5'-GATCCGACXXXXXXXXXXXXXXXXXXNNNNNNNNNNNNNNNNNN
AAGTTG
```

```
                                            (SEQ ID NO: 13)
GCTGXXXXXXXXXXXXXXXXXXNNNNNNNNNNNNNNNNNNTTCAACC
TAG-5'
```

Wherein X and N may be any of A, C, G or T.

We used two approaches to this:
  (i) Bacterial transformation, tagged-plasmid purification and restriction digest to release 50 bp cohesive ditags;
  (ii) Direct PCR on the ligation reaction followed by restriction digest of the PCR products to release 50 bp cohesive ditags.

2-5-1 Transformation and Propagation; Preparation of Tagged-plasmids (See FIG. 1)

1 μl of the ligation reaction (Section 2-4) were transformed per 50 μl of electrocompetent TOP10 cells (Invitrogen) by electroporation. Recovered in 1 ml SOC media at 37 C for 1 hr, then plated out several dilutions on LB agar+ampicillin for QC and titering.

QC (Quality Check): plasmid DNA was prepared from several colonies and tested by digestion with BamHI: tagged-plasmids release a 50 bp cohesive ditag.

This process was then scaled-up by plating the remaining culture on large agar plates, and performing maxipreps using Qiagen HiSpeed Plasmid Maxi kit.

As an example, approximately 5,000 colonies was processed to yield at least 40 ug of tagged-plasmid DNA.

Figure 5:
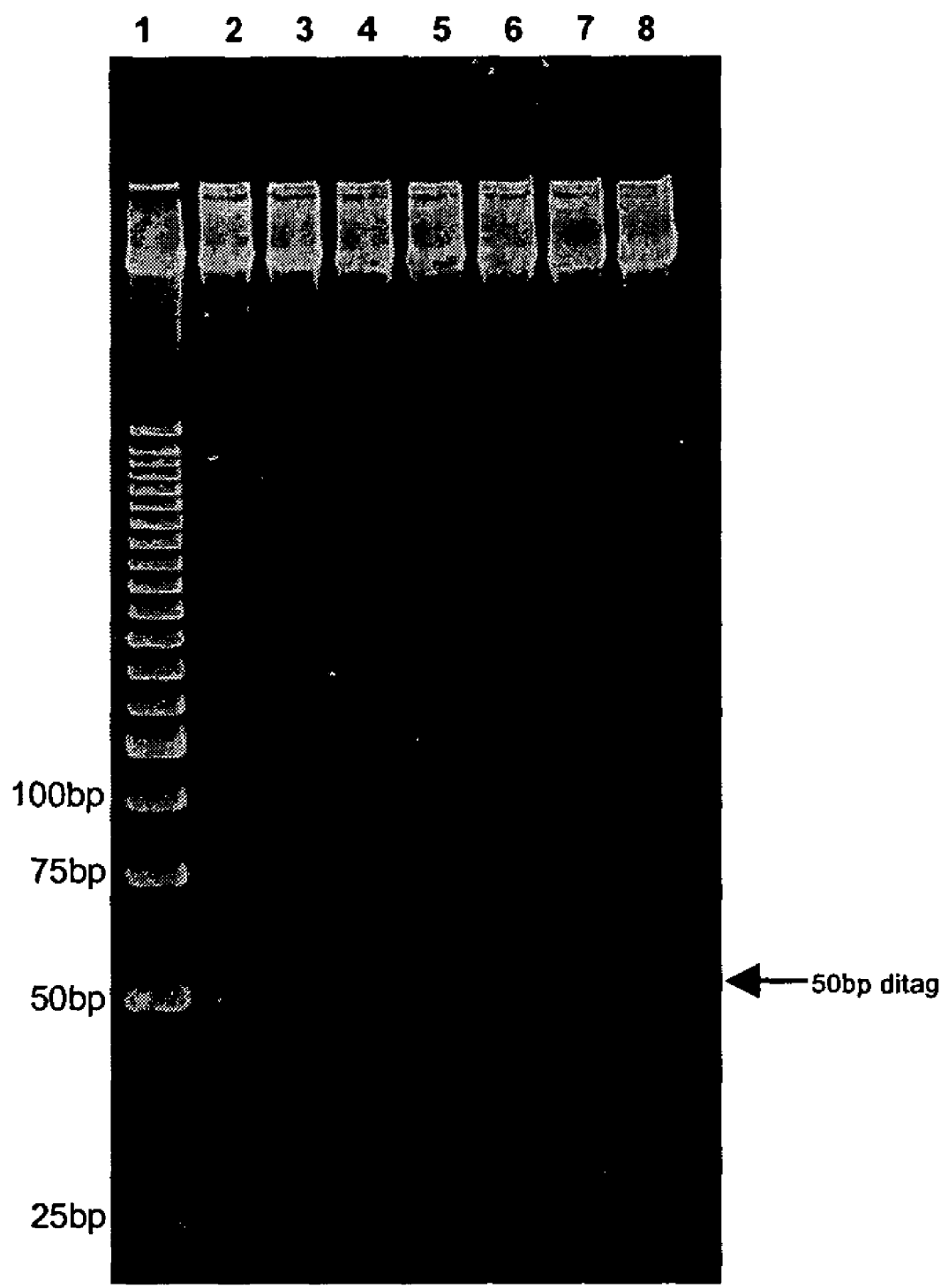
FIG. 5 is an electrophoresis gel related to the preparation of GIS ditags. The plasmid DNA of GIS ditag library is digested with BamHI. The 50 bp ditag fragments are separated and purified from the vector using a 10% polyacrylamide gel. Lane 1: DNA size markers. Lane 2-8: formation of 50 bp GIS ditags.

This plasmid DNA was then BamHI-digested to generate 50 bp cohesive ditags (see FIG. 5 as example result).

2-5-2 PCR-based Retrieval of Cohesive Ditags (See FIG. 2

PCR was performed on the ligation reaction using primers PMR003 and PMR004 that bind to vector sequences flanking the ditags.

```
PMR003:                                     (SEQ ID NO: 7)
5'-GTAAAACGACGGCCAGT-3'
```

```
PMR004:                                     (SEQ ID NO: 8)
5'-GGAAACAGCTATGACCATG-3'
```

The amount of starting material was determined empirically by doing a series of dilutions and choosing the conditions that result in a clean, specific PCR product of approximately 200 bp

| | |
|---|---|
| (e.g. 1:200) diluted ligation reaction | 5.0 μL |
| 10× HiFi buffer | 2.0 μL |
| 10 mM dNTP | 0.4 μL |
| PMR003 (100 ng/μL) | 1.0 μL |
| PMR004 (100 ng/μL) | 1.0 μL |
| Eppendorf TripleMaster polymerase | 0.2 μL |
| dH2O | 10.4 μL |

(the HiFi buffer was the reaction buffer provided with the Eppendorf TripleMaster enzyme)

Figure 6:
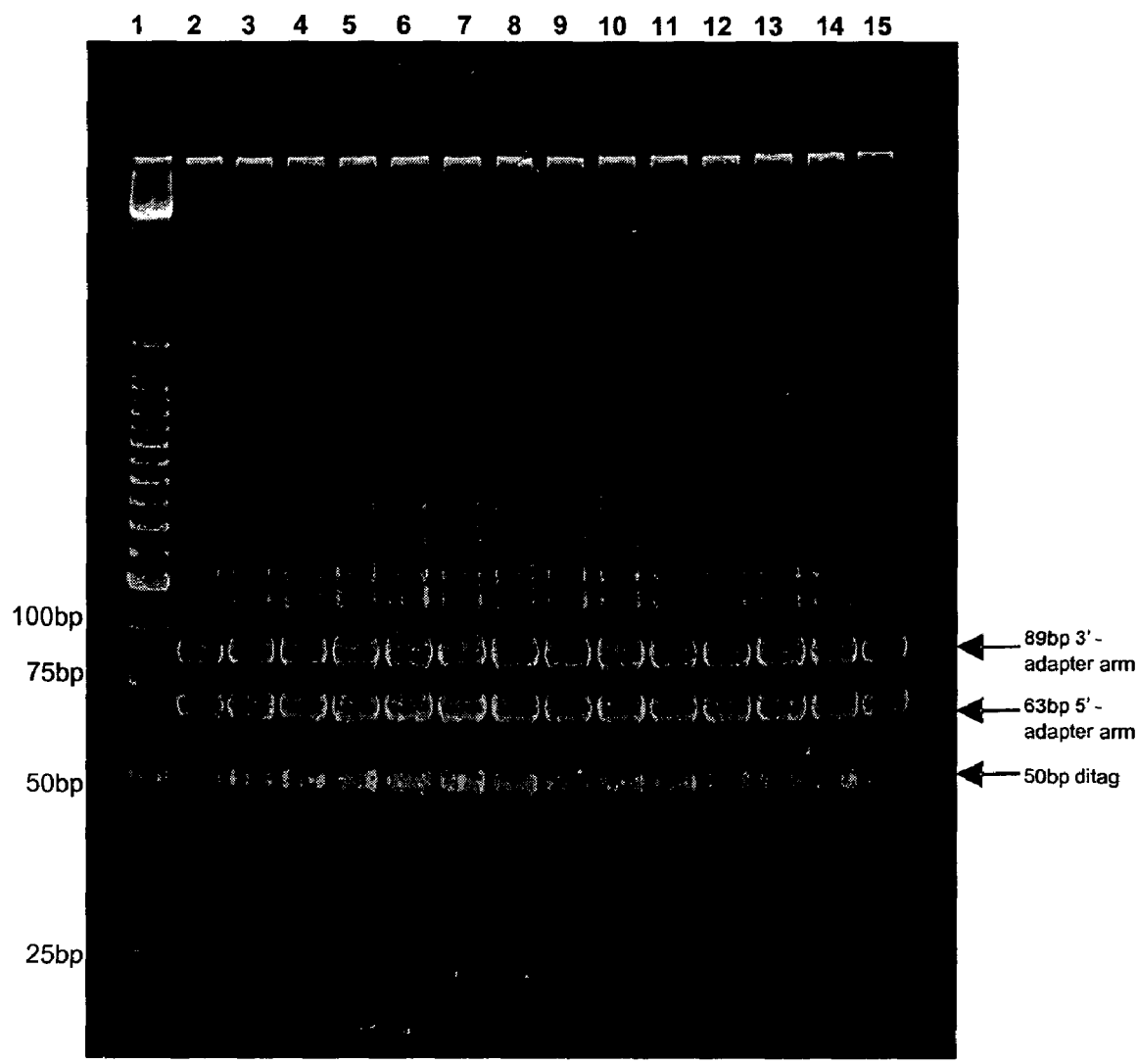
FIG. 6 is an electrophoresis gel related to the preparation of GIS ditags by PCR. The ditag-containing PCR fragments generated from the GIS full-length cDNA library are digested by BamHI. The 50 bp ditag fragments are separated and purified from adaptor arms in 10% polyacrylamide gel. Lane 1: DNA size markers. Lane 2-15: large scale preparation of 50 bp GIS ditags.

Thermo-cycling conditions:
Step 1: 95 C×2 min
Step 2: 95 C×30 sec
Step 3: 55 C×1 min
Step 4: 72 C×30 sec Go to step 2, repeat steps (2-4) 24×
Step 5: 72 C×4 min
16° C. forever The PCR products were analyzed on a 1.5% agarose gel.
For negative controls, the PCR reaction was performed using (i) no template, and (ii) no ligase. To obtain sufficient 200 bp PCR product for subsequent 50 bp cohesive ditag production, the reaction was scaled-up: do 96 PCR reactions using a 96-well PCR plate; this generates approx. 50 ug of 200 bp ditag. The individual PCR reactions are then combined and ethanol precipitated before Bam HI digest to generate 50 bp cohesive ditags (see FIG. 6 as an example result).

3. GIS Library
3-1. Tagged-plasmid Preparation

This applies only to the bacterial transformation-based approach (see Section 2-5-1).

3-2. BamHI Digestion and Purification of GIS Tags
3-2-1 BamHI Digestion of Tagged-plasmids (Section 2-5-1) Released 50 bp Cohesive Ditags:

| DNA (tagged-plasmids) | 40 μg |
| 10× unique BamHI buffer (NEB) | 100 μL |
| 100× BSA | 10 μL |
| BamHI (20 U/μL, NEB) | 10 μL |
| dH2O | to 1 mL |

The choice of value of 40 μg of DNA (tagged-plasmids) was arbitrary.

Aliquots were divided into 10×100 ul for more efficient digestion, and incubated at 37 C, for 4 hrs.

After digest, they were inactivated at 65 C, for 15 min, then phenol-chloroform extraction and ethanol precipitation were performed. Then, the pellet comprising 50 bp cohesive ditags and the rest of the cleavage products after the BamHI digest was resuspended in LoTE buffer for gel-purification.

3-2-2 BamHI Digestion of or 200 bp Ditags Retrieved by PCR (Section 2-5-2) released 50 bp cohesive ditags:

| DNA (PCR products) | 40 μg |
| 10× unique BamHI buffer (NEB) | 100 μL |
| 100× BSA | 10 μL |
| BamHI (20 U/μL, NEB) | 10 μL |
| dH2O | to 1 mL |

The choice of value of 40 μg of DNA (tagged-plasmids) was arbitrary.

Aliquots were divide into 10×100 ul for more efficient digestion, incubated at 37 C, for 4 hrs.

After digest, they were inactivated at 65 C, for 15 min, then phenol-chloroform extraction and ethanol precipitation were performed. Then, the pellet comprising 50 bp cohesive ditags and the rest of the cleavage products after the BamHI digest was resuspended in LoTE buffer for gel-purification.

3-3 Gel-purification of 50 bp Cohesive Ditags

The BamHI-digested DNA according to both section 3-2-1 or 3-2-2 was separated on a large (Hoefer Ruby 600, 15×15 cm, 1.5 mm thick) 10% polyacrylamide gel. Electrophoresis proceeded at 200V for approx. 2 hrs until the Bromophenol Blue (standard tracking dye) band almost reached the bottom of the gel. The gel was stained in SYBR Green I (Molecular Probes, Inc.) for 30 min before visualisation and excision of the 50 bp cohesive ditags.

At this stage it is convenient not to load more than 5 μg per lane, or fluorescence quenching occurs.

The 50 bp cohesive ditags were excised and collected into 0.6 ml microfuge tubes (2 gel pieces per tube) which have been pierced at the bottom with a 21 G needle. This pierced tube was placed inside a 1.7 ml microfuge tube, and centrifuged at 12K g, 4 C for 2-5 min. The gel pieces were thus shredded and collected in the 1.7 ml tube.

150 μl of LoTE:NH4OAc (125:25) were added to each tube and left overnight at 4 C to elute. The next day, the eluate was collected with the aid of microspin filter units (SpinX, Costar), and ethanol precipitation performed to retrieve the purified 50 bp ditags, which were resuspended in LoTE. Starting from 70 μg 200 bp ditag, we expected to retrieve several hundred ng of 50 bp ditag.

3-4. Ditag Concatenation and Gel-purification

Some optimization (ligation time, amount of starting material) may be necessary to ensure that the concatenation of the 50 bp ditags results in a smear of products ranging from approx. 300 bp to >1000 bp. The conditions below are suggested as a starting point:

| 50 bp cohesive ditags | 150-500 ng |
| 5× buffer (with PEG; BRL) | 2.0 μL |
| T4 DNA ligase (5 U/μL) | 1.0 μL |
| dH2O | to 10 μL |

Incubated at 16° C. for 1 hr.

Loading buffer was added and the entire sample heated at 65 C for 15 min. The sample loaded in a single well of an 8% polyacrylamide minigel and run at 200V for about 1 hr, or until Bromophenol Blue was about 2 cm from bottom.

The smear of ligation products can be excised as 2 or more fractions, eg. 200-500 bp; 500-1000 bp; >1000 bp.

Elution of DNA from the gel pieces was performed as detailed in Section 3-3. The eluate was extracted with phenol-chloroform then ethanol precipitated. Resuspend the DNA pellet in 6 ul LoTE.

3-5. Cloning of Concatemers

Figure 8:
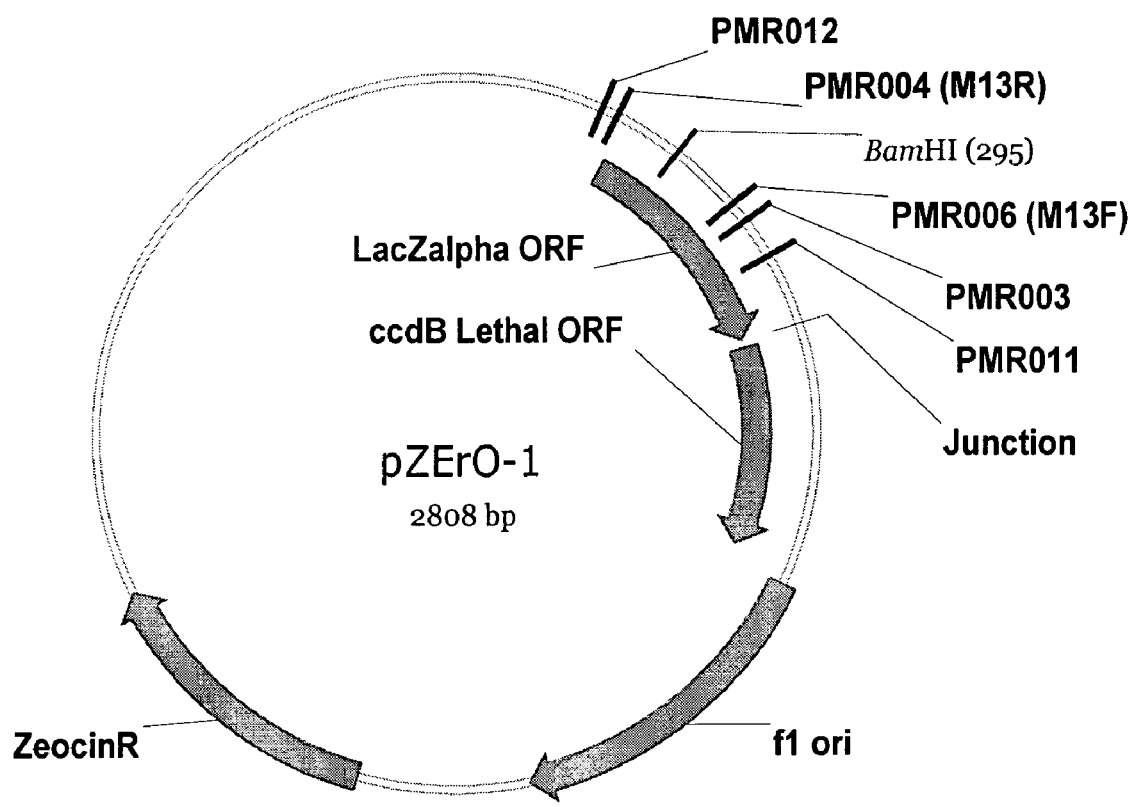
FIG. 8 shows the commercial pZErO-1 vector construct (Invitrogen) The positions of the various sequencing/PCR primer binding sites (PMR003, PMR004, PMR011 and PMR012) are shown.

The cloning vector was prepared by digesting 2 ug of pZErO-1 plasmid DNA (Invitrogen) (FIG. 8) (FIG. 8 shows the sequencing/PCR primer binding sites) with 10 units of BamHI for 3 hours at 37 C. The digested DNA was phenol-chloroform extracted and ethanol precipitated, then resuspended in LoTE at a concentration of 33 ng/μl. The ligation reaction was performed as follows:

| Concatemer DNA | 6.0 μL |
| BamHI/pZErO-1 | 1.0 μL |
| 5× ligase buffer | 2.0 μL |
| T4 DNA ligase (5 U/μL) | 1.0 μL |

Incubated at 16° C. overnight.

The vector self-ligation was also performed in parallel as a control.

The ligation products were purified before electroporation. The phenol-chloroform extraction was followed by ethanol precipitation; the pellet was washed 3 times with 75% ethanol before re-suspending in 12 μl TE (0.1×). 1 μl of this DNA was used to transform 50 μl of electro-competent TOP10 bacterial cells. After recovery (see also Section 2-5-1), 50 μl were plated on a small agar plate (containing Low Salt LB agar (Lennox L) plus Zeocin (50 μg/ml) and IPTG (50 μg/ml) and incubated overnight at 37 C. As a background control, bacteria were plated out that have been similarly transformed with the vector self-ligation reaction above. (IPTG is optional when using TOP 10 cells but may reduce background).

3-6. GIS Library QC (Quality Check)

The following day, 10-30 colonies were picked to check for insert size by PCR. For each reaction, a single colony was picked into a PCR tube containing:

| | |
|---|---|
| 10× HiFi buffer | 2.0 μL |
| 10 mM dNTP | 0.4 μL |
| PMR003 (100 ng/ul) | 1.0 μL |
| PMR004 (100 ng/ul) | 1.0 μL |
| Eppendorf TripleMaster polymerase | 0.2 μL |
| dH2O | 11.4 μL |

Thermo-cycling conditions:
Step 1: 95 C×2 min
Step 2: 95 C×30 sec
Step 3: 55 C×1 min
Step 4: 72 C×3 min
Go to step 2, repeat steps (2-4) 24×
Step 5: 72 C×4 min
16° C. forever The PCR products were visualized on 1% agarose gel. A typical result is shown in FIG. 9.

The primer pair PMR003/PMR004 (SEQ ID NO:7/SEQ ID NO:8) gives a band of approx. 220 bp in the absence of any cloned insert. If the quality of the library thus produced appears good, the remaining transformation mixture can be plated out (Section 3-5) on large agar plates in preparation for DNA sequencing analysis.

The primer pair PMR003/PMR004 is also convenient for checking the quality of the library, but for the actual preparation of PCR templates for sequencing, primer pair PMR012/PMR003 (SEQ ID NO:11/SEQ ID NO:7) were preferred (see Section 4-2).

```
                                           (SEQ ID NO: 11)
PMR012:   5'-AGCGGATAACAATTTCACACAGG-3'.
```

4. Sequencing Analysis of GIS Tags
4-1. Library Plating and Colony Picking

The transformed TOP10 (Invitrogen) bacteria cells were plated out on 22×22 cm agar plates with colony density less than 3,000 per plate. Individual colonies were picked and cultured in 384-well plates with LB plus Zeocin (see above in section 3.5) at 37° C. overnight. Multiple copies of 384-well plates are replicated and stored in −80° C.

4-2. Template Preparation

Bacterial cultures in 384-well plates were inoculated in pre-mixed PCR cocktails. PCR was performed using primer pair PMR012/PMR003.

This primer pair gives a band of 245 bp in the absence of any concatemer insert. Nonetheless, this set of primers is preferred as it allows the use of sequencing primers PMR004 (M13 reverse; 68 bp from BamHI site) and PMR006 (SEQ ID NO:9)(M13 forward; 87 bp from BamHI site).

```
PMR006:   5'-TAATACGACTCACTATAGGG-3' (SEQ ID NO: 9)
```

4-3. Sequencing

PCR templates were sequenced using the sequencing primers PMR004 and PMR006 to sequence in both directions.

Example 3

The GIS analysis method according to any embodiment of the invention is a complete gene discovery platform. It combines full-length cDNA library construction, cDNA tag sequencing, genome mapping and annotation into one operation from the same starting materials. For example, to study the genes expressed in human stem cells, we start with the stem cell mRNA, construct a stem cell GIS full-length cDNA library, and then the GIS library. We will only need to sequence 50,000 clones of the GIS library to reveal over a million transcripts. Such deep sampling will allow us to capture nearly all unique transcripts expressed in the human stem cell transcriptome. Each of the GIS ditags can be specifically mapped to the genome and therefore define the structural regions of the corresponding genes on the chromosomes. Most of the GIS ditags map to known genes on chromosomes and the counts of the GIS ditags provide the measurement of expression activity. Some of the GIS ditags may map to desert ("no gene") regions of the genome, which may suggest the identification of new genes that are expressed in the stem cell transcriptome. In such a way the genome annotation for genes is further refined by this whole transcriptome-to-whole genome approach. Based on the GIS ditag sequences, these putative new genes can be readily cloned from the original GIS full-length cDNA library.

We can apply this GIS gene discovery system not only to human stem cells, but also to all other biological systems, such as development of cells, tissues and organs of human and model organisms.

What is claimed is:

1. A method for preparing at least one ditag comprising the steps of:
   (i) producing at least one full-length cDNA transcript, said transcript having a 5' terminus including the starting point of the full-length cDNA transcript and a 3' terminus including the ending point of the full-length cDNA transcript;
   (ii) cleaving the full-length cDNA transcript at its 5' terminus to extract a 5' tag 8-20 base pairs (bp) in length, said 5' tag having a 5' end and a 3' end and including the starting point of the full-length cDNA transcript, and cleaving the full-length cDNA transcript at its 3' terminus to extract a 3' tag 8-20 bp in length, said 3' tag having a 5' end and a 3' end and including the ending point of the full-length cDNA transcript; and
   (iii) generating at least one ditag by ligating the 3' end of the 5' tag to the 5' end of the 3' tag.

2. A method of mapping a gene on a genome, comprising:
   preparing at least one ditag according to the method of claim 1, and
   mapping the 5' and 3' tags of the at least one ditag on a genome; and
   defining the entire structural region of the corresponding gene on the genome, wherein the region being defined includes exons and introns of the gene.

3. A method of gene discovery comprising:
   preparing at least one ditag according to the method of claim 1,
   determining the sequence of the at least one ditag and comparing the sequence of the at least one ditag with a genome sequence and a gene database;
   wherein detecting matching of the sequence of the 5' and 3' tags of the at least one ditag with the genome sequence but detecting no match with one or more gene databases indicates a new gene.

4. The method of claim 3, further comprising recovering a full-length cDNA corresponding to the at least one ditag by PCR or directly from target RNA samples by RT-PCR.

5. A method for preparing at least one ditag comprising the steps of:
   (i) providing at least one full-length cDNA transcript having a 5' terminus including the starting point of the full-length cDNA transcript and a 3' terminus including the ending point of the full-length cDNA transcript, and flanked by two adapters;
   (ii) cleaving the full-length cDNA transcript at its 5' terminus to extract a 5' tag 8-20 base pairs (bp) in length, said 5' tag having a 5' end and a 3' end and including the starting point of the full length cDNA transcript and an adapter, and cleaving the full-length cDNA transcript at its 3' terminus to extract a 3' tag 8-20 by in length, said 3' tag having a 5' end and a 3' end and including the ending point of the full length cDNA transcript and an adapter; and
   (iii) generating at least one ditag flanked by two adapters by ligating the 3' end of the 5' tag to the 5' end of the 3' tag.

6. The method of claim 5, further comprising the step of creating a concatemer of ditags.

7. The method of claim 5, further comprising including the at least one ditag flanked by the adapters in a vector.

8. The method of claim 7, wherein the vector further comprises two adapters flanking the at least one ditag, wherein each adapter includes at least one restriction site.

9. The method of claim 8, wherein each adapter comprises at least a first restriction site which is an asymmetric restriction site and a second restriction site.

10. The method of claim 9, wherein the backbone of the vector does not comprise the asymmetric restriction site or the second restriction site.

11. The method of claim 10, wherein the asymmetric restriction site is a type II restriction site.

12. The method of claim 7, wherein each adapter comprises at least: a first restriction site which is a type II restriction site and at least a second restriction site, and wherein the backbone of the vector does not comprise the type II restriction site or the second restriction site.

13. The method of claim 12, wherein the type II restriction site is a MmeI site.

14. The method of claim 7, wherein the vector comprises SEQ ID No:18.

15. The method of claim 5, further comprising the step of determining the nucleotide sequence of the at least one ditag.

16. The method of claim 5, further comprising:
determining the sequence of the at least one ditag; and
mapping the 5' and 3' tags of the at least one ditag nucleotide sequence to a database comprising genomic sequences.

17. The method of claim 5, wherein each adapter comprises at least one restriction site and step (ii) includes adding at least one restriction enzyme capable of recognizing the at least one restriction site to the full-length cDNA transcript flanked by the two adapters from step (i).

18. The method of claim 17, wherein the at least one restriction site is an asymmetric recognition site.

19. The method of claim 18, wherein the asymmetric recognition site is a restriction endonuclease asymmetric cleavage site sequence recognizable by a type II restriction enzyme selected from the group consisting of AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II.

20. The method of claim 18, wherein the asymmetric recognition site is a homing endonuclease asymmetric recognition site sequence-recognizable by a homing endonuclease selected from the group consisting of: I-CeuI, PI-SceI, PI-PspI and I-SceI.

21. The method of claim 5 wherein each adapter comprises at least one restriction site which is a MmeI recognition site; and step (ii) comprises
cleaving the full-length cDNA transcript flanked by the two adapters from step (i) with MmeI.

22. The method of claim 5, wherein the at least one ditag is 34-38 nucleotides in length.

* * * * *

SEQUENCE LISTING

```
<160> NUMBER OF SEQ ID NOS: 29

<210> SEQ ID NO 1
<211> LENGTH: 33
<212> TYPE: DNA
<213> ORGANISM: Artificial
<220> FEATURE:
<223> OTHER INFORMATION: oligonucleotide primer with homology to
      bacterial cloning vector
<220> FEATURE:
<221> NAME/KEY: misc_feature
<222> LOCATION: (1)..(33)
<223> OTHER INFORMATION: n is a,c,g, or t
<220> FEATURE:
<221> NAME/KEY: misc_feature
<222> LOCATION: (1)..(33)
<223> OTHER INFORMATION: v is a,c,g

<400> SEQUENCE: 1
gagctccttc tggagttttt ttttttttt tvn                             33

<210> SEQ ID NO 2
```

```
<211> LENGTH: 30
<212> TYPE: DNA
<213> ORGANISM: Artificial
<220> FEATURE:
<223> OTHER INFORMATION: oligonucleotide primer with homology to
      bacterial cloning vector
<220> FEATURE:
<221> NAME/KEY: misc_feature
<222> LOCATION: (1)..(30)
<223> OTHER INFORMATION: n is a,t,c or g

<400> SEQUENCE: 2
aattcgcggc cgcttggatc cgacnnnnnn                                          30

<210> SEQ ID NO 3
<211> LENGTH: 20
<212> TYPE: DNA
<213> ORGANISM: Artificial
<220> FEATURE:
<223> OTHER INFORMATION: oligonucleotide primer with homology to
      bacterial cloning vector

<400> SEQUENCE: 3
gtcggatcca agcggccgcg                                                     20

<210> SEQ ID NO 4
<211> LENGTH: 30
<212> TYPE: DNA
<213> ORGANISM: Artificial
<220> FEATURE:
<223> OTHER INFORMATION: oligonucleotide primer with homology to
      bacterial cloning vector
<220> FEATURE:
<221> NAME/KEY: misc_feature
<222> LOCATION: (1)..(30)
<223> OTHER INFORMATION: n is a,t,c or g

<400> SEQUENCE: 4
aattcgcggc cgcttggatc cgacgnnnnn                                          30

<210> SEQ ID NO 5
<211> LENGTH: 19
<212> TYPE: DNA
<213> ORGANISM: Artificial
<220> FEATURE:
<223> OTHER INFORMATION: oligonucleotide primer with homology to
      bacterial cloning vector

<400> SEQUENCE: 5
tcgacccagg atccaactt                                                      19

<210> SEQ ID NO 6
<211> LENGTH: 13
<212> TYPE: DNA
<213> ORGANISM: Artificial
<220> FEATURE:
<223> OTHER INFORMATION: oligonucleotide primer with homology to
      bacterial cloning vector
<220> FEATURE:
<221> NAME/KEY: misc_feature
<222> LOCATION: (1)..(13)
<223> OTHER INFORMATION: phosporylation

<400> SEQUENCE: 6
gttggatcct ggg                                                            13

<210> SEQ ID NO 7
<211> LENGTH: 17
<212> TYPE: DNA
<213> ORGANISM: Artificial
```

```
<220> FEATURE:
<223> OTHER INFORMATION: oligonucleotide primer with homology to
      bacterial cloning vector

<400> SEQUENCE: 7
gtaaaacgac ggccagt                                                    17

<210> SEQ ID NO 8
<211> LENGTH: 19
<212> TYPE: DNA
<213> ORGANISM: Artificial
<220> FEATURE:
<223> OTHER INFORMATION: oligonucleotide primer with homology to
      bacterial cloning vector

<400> SEQUENCE: 8
ggaaacagct atgaccatg                                                  19

<210> SEQ ID NO 9
<211> LENGTH: 20
<212> TYPE: DNA
<213> ORGANISM: Artificial
<220> FEATURE:
<223> OTHER INFORMATION: oligonucleotide primer with homology to
      bacterial cloning vector

<400> SEQUENCE: 9
taatacgact cactataggg                                                 20

<210> SEQ ID NO 10
<211> LENGTH: 22
<212> TYPE: DNA
<213> ORGANISM: Artificial
<220> FEATURE:
<223> OTHER INFORMATION: oligonucleotide primer with homology to
      bacterial cloning vector

<400> SEQUENCE: 10
gatgtgctgc aaggcgatta ag                                              22

<210> SEQ ID NO 11
<211> LENGTH: 23
<212> TYPE: DNA
<213> ORGANISM: Artificial
<220> FEATURE:
<223> OTHER INFORMATION: oligonucleotide primer with homology to
      bacterial cloning vector

<400> SEQUENCE: 11
agcggataac aatttcacac agg                                             23

<210> SEQ ID NO 12
<211> LENGTH: 48
<212> TYPE: DNA
<213> ORGANISM: Artificial
<220> FEATURE:
<223> OTHER INFORMATION: Oligonucleotide with homology to a bacteria
      cloning vector
<220> FEATURE:
<221> NAME/KEY: misc_feature
<222> LOCATION: (1)..(48)
<223> OTHER INFORMATION: n is a,t,c or g

<400> SEQUENCE: 12
gatccgacnn nnnnnnnnn nnnnnnnnn nnnnnnnnn nnaagttg                     48

<210> SEQ ID NO 13
<211> LENGTH: 48
```

```
<212> TYPE: DNA
<213> ORGANISM: Artificial
<220> FEATURE:
<223> OTHER INFORMATION: Oligonucleotide with homology to a bacteria
      cloning vector
<220> FEATURE:
<221> NAME/KEY: misc_feature
<222> LOCATION: (1)..(48)
<223> OTHER INFORMATION: n is a,t,c or g

<400> SEQUENCE: 13
gatccaactt nnnnnnnnnn nnnnnnnnnn nnnnnnnnnn nnnngtcg                48

<210> SEQ ID NO 14
<211> LENGTH: 29
<212> TYPE: DNA
<213> ORGANISM: Artificial
<220> FEATURE:
<223> OTHER INFORMATION: Oligonucleotide primer with homology to a
      bacteria cloning vector
<220> FEATURE:
<221> NAME/KEY: misc_feature
<222> LOCATION: (1)..(29)
<223> OTHER INFORMATION: phosphorylation

<400> SEQUENCE: 14
cgctctcctg taccgaccct gccgcttac                                      29

<210> SEQ ID NO 15
<211> LENGTH: 29
<212> TYPE: DNA
<213> ORGANISM: Artificial
<220> FEATURE:
<223> OTHER INFORMATION: Oligonucleotide primer with homology to a
      bacteria cloning vector
<220> FEATURE:
<221> NAME/KEY: misc_feature
<222> LOCATION: (1)..(29)
<223> OTHER INFORMATION: phosphorylation

<400> SEQUENCE: 15
aactatcgtc ttgagaccaa cccggtaag                                      29

<210> SEQ ID NO 16
<211> LENGTH: 24
<212> TYPE: DNA
<213> ORGANISM: Artificial
<220> FEATURE:
<223> OTHER INFORMATION: Oligonucleotide adapter with homology to a
      bacteria cloning vector

<400> SEQUENCE: 16
aattctcgag cggccgcgat atcg                                           24

<210> SEQ ID NO 17
<211> LENGTH: 24
<212> TYPE: DNA
<213> ORGANISM: Artificial
<220> FEATURE:
<223> OTHER INFORMATION: Oligonucleotide adapter with homology to a
      bacteria cloning vector
<220> FEATURE:
<221> NAME/KEY: misc_feature
<222> LOCATION: (1)..(24)
<223> OTHER INFORMATION: phosphorylation

<400> SEQUENCE: 17
aattcgatat cgcggccgct cgag                                           24

<210> SEQ ID NO 18
```

<211> LENGTH: 3404
<212> TYPE: DNA
<213> ORGANISM: Artificial
<220> FEATURE:
<223> OTHER INFORMATION: bacterial cloning vector

<400> SEQUENCE: 18

```
gggcgaattc tcgagcggcc gcggatccga cgagagcgcc tgcgtacggc tcgccgcggt      60
ggctggcgct acttcggagg agcccgacgc ggcgcggtcg tttttataca ttcccgcgcg     120
gaggcaacgg aagggcgggg cgcctcgtga ttaggccgcg gaggtcacag gctctgttgt     180
catgaaggtg aaaattaaat gttggaatgg tgtggccact tggctctggg tagccaatga     240
tgagaactgc ggcatctgca ggatggcgtt taatggctgc tgtccagact gtaaggtgcc     300
tggtgatgac tgccccctcg tgtggggaca gtgctcccac tgcttccaca tgcactgcat     360
cctcaagtgg ctgaatgcgc agcaggtgca gcagcactgc cccatgtgtc gccaggagtg     420
gaagttcaaa gagtgaagcc cgtgccgtgc cacttccctc tcctgtgctg tgccaggctc     480
agccccttcc ctccctcccc tcccccagat acagcacccc aagtcccctc cacacagcac     540
agtggtgccc agagatctcg gtctgtgccg gggacaagga tgctttctgt ttggctggga     600
caaggttgaa aggagctttg ctgactgttt tgttttccca tcacattgac actttattca     660
ataagtaaaa ctcattacag ttccaagtcg gatcctgggt cgacctgcag gcatgcaagc     720
ttgagtattc tatagtgtca cctaaatagc ttggcgtaat catggtcata gctgtttcct     780
gtgtgaaatt gttatccgct cacaattcca cacaacatac gagccggaag cataaagtgt     840
aaagcctggg gtgcctaatg agtgagctaa ctcacattaa ttgcgttgcg ctcactgccc     900
gctttccagt cgggaaacct gtcgtgccag ctgcattaat gaatcggcca acgcgcgggg     960
agaggcggtt tgcgtattgg gcgctcttcc gcttcctcgc tcactgactc gctgcgctcg    1020
gtcgttcggc tgcggcgagc ggtatcagct cactcaaagg cggtaatacg gttatccaca    1080
gaatcagggg ataacgcagg aaagaacatg tgagcaaaag gccagcaaaa ggccaggaac    1140
cgtaaaaagg ccgcgttgct ggcgtttttc cataggctcc gcccccctga cgagcatcac    1200
aaaaatcgac gctcaagtca gaggtggcga acccgacag gactataaag ataccaggcg    1260
tttccccctg gaagctccct cgtgcgctct cctgttccga ccctgccgct taccggatac    1320
ctgtccgcct ttctcccttc gggaagcgtg gcgctttctc atagctcacg ctgtaggtat    1380
ctcagttcgg tgtaggtcgt tcgctccaag ctgggctgtg tgcacgaacc ccccgttcag    1440
cccgaccgct gcgccttatc cggtaactat cgtcttgaga ccaacccggt aagacacgac    1500
ttatcgccac tggcagcagc cactggtaac aggattagca gagcgaggta tgtaggcggt    1560
gctacagagt tcttgaagtg gtggcctaac tacggctaca ctagaaggac agtatttggt    1620
atctgcgctc tgctgaagcc agttaccttc ggaaaaagag ttggtagctc ttgatccggc    1680
aaacaaacca ccgctggtag cggtggtttt tttgtttgca agcagcagat tacgcgcaga    1740
aaaaaaggat ctcaagaaga tcctttgatc ttttctacgg ggtctgacgc tcagtggaac    1800
gaaaactcac gttaagggat tttggtcatg agattatcaa aaaggatctt cacctagatc    1860
cttttaaatt aaaaatgaag ttttaaatca atctaaagta tatatgagta aacttggtct    1920
gacagttacc aatgcttaat cagtgaggca cctatctcag cgatctgtct atttcgttca    1980
tccatagttg cctgactccc cgtcgtgtag ataactacga tacgggaggg cttaccatct    2040
ggccccagtg ctgcaatgat accgcgagac ccacgctcac cggctccaga tttatcagca    2100
ataaaccagc cagccggaag ggccgagcgc agaagtggtc ctgcaacttt atccgcctcc    2160
```

```
atccagtcta ttaattgttg ccgggaagct agagtaagta gttcgccagt taatagtttg    2220
cgcaacgttg ttggcattgc tacaggcatc gtggtgtcac gctcgtcgtt tggtatggct    2280
tcattcagct ccggttccca acgatcaagg cgagttacat gatcccccat gttgtgcaaa    2340
aaagcggtta gctccttcgg tcctccgatc gttgtcagaa gtaagttggc cgcagtgtta    2400
tcactcatgg ttatggcagc actgcataat tctcttactg tcatgccatc cgtaagatgc    2460
ttttctgtga ctggtgagta ctcaaccaag tcattctgag aatagtgtat gcggcgaccg    2520
agttgctctt gcccggcgtc aatacgggat aataccgcgc cacatagcag aactttaaaa    2580
gtgctcatca ttggaaaacg ttcttcgggg cgaaaactct caaggatctt accgctgttg    2640
agatccagtt cgatgtaacc cactcgtgca cccaactgat cttcagcatc ttttactttc    2700
accagcgttt ctgggtgagc aaaaacagga aggcaaaatg ccgcaaaaaa gggaataagg    2760
gcgacacgga aatgttgaat actcatactc ttcctttttc aatattattg aagcatttat    2820
cagggttatt gtctcatgag cggatacata tttgaatgta tttagaaaaa taaacaaata    2880
ggggttccgc gcacatttcc ccgaaaagtg ccacctgacg tctaagaaac cattattatc    2940
atgacattaa cctataaaaa taggcgtatc acgaggccct ttcgtctcgc gcgtttcggt    3000
gatgacggtg aaaacctctg acacatgcag ctcccggaga cggtcacagc ttgtctgtaa    3060
gcggatgccg ggagcagaca gcccgtcag ggcgcgtcag cgggtgttgg cgggtgtcgg    3120
ggctggctta actatgcggc atcagagcag attgtactga gagtgcacca tatgcggtgt    3180
gaaataccgc acagatgcgt aaggagaaaa taccgcatca ggcgccattc gccattcagg    3240
ctgcgcaact gttgggaagg gcgatcggtg cgggcctctt cgctattacg ccagctggcg    3300
aaagggggat gtgctgcaag gcgattaagt tgggtaacgc cagggttttc ccagtcacga    3360
cgttgtaaaa cgacggccag tgaattgtaa tacgactcac tata                     3404
```

<210> SEQ ID NO 19
<211> LENGTH: 10
<212> TYPE: DNA
<213> ORGANISM: Artificial
<220> FEATURE:
<223> OTHER INFORMATION: mammalian p53 consensus sequence
<220> FEATURE:
<221> NAME/KEY: misc_feature
<223> OTHER INFORMATION: r is a purine (A or G)
<220> FEATURE:
<221> NAME/KEY: misc_feature
<223> OTHER INFORMATION: w is  A or T
<220> FEATURE:
<221> NAME/KEY: misc_feature
<223> OTHER INFORMATION: y is a pyrimidine (C or T)

<400> SEQUENCE: 19 rrrcwwgyyy                                                              10

<210> SEQ ID NO 20
<211> LENGTH: 20
<212> TYPE: DNA
<213> ORGANISM: Artificial
<220> FEATURE:
<223> OTHER INFORMATION: mammalian p53 consensus sequence

<400> SEQUENCE: 20
gaacatgtcc caacatgttg                                                   20

<210> SEQ ID NO 21
<211> LENGTH: 20
<212> TYPE: DNA
<213> ORGANISM: Artificial

```
<220> FEATURE:
<223> OTHER INFORMATION: mammalian p53 consensus sequence

<400> SEQUENCE: 21
agacaagccc gggcaaggcc                                                          20

<210> SEQ ID NO 22
<211> LENGTH: 2770
<212> TYPE: DNA
<213> ORGANISM: Artificial
<220> FEATURE:
<223> OTHER INFORMATION: Bacterial Cloning Vector

<400> SEQUENCE: 22
gggcgaattc gatatcgcgg ccgcgaggag tatggatccg actcgagtcg gatcctggct      60
cctcgtcgac ctgcaggcat gcaagcttga gtattctata gtgtcaccta aatagcttgg    120
cgtaatcatg gtcatagctg tttcctgtgt gaaattgtta tccgctcaca attccacaca    180
acatacgagc cggaagcata aagtgtaaag cctggggtgc ctaatgagtg agctaactca    240
cattaattgc gttgcgctca ctgcccgctt tccagtcggg aaacctgtcg tgccagctgc    300
attaatgaat cggccaacgc gcggggagag gcggtttgcg tattgggcgc tcttccgctt    360
cctcgctcac tgactcgctg cgctcggtcg ttcggctgcg gcgagcggta tcagctcact    420
caaaggcggt aatacggtta tccacagaat caggggataa cgcaggaaag aacatgtgag    480
caaaaggcca gcaaaaggcc aggaaccgta aaaaggccgc gttgctggcg tttttcgata    540
ggctccgccc ccctgacgag catcacaaaa atcgacgctc aagtcagagg tggcgaaacc    600
cgacaggact ataaagatac caggcgtttc ccctggaag  ctccctcgtg cgctctcctg    660
taccgaccct gccgcttacc ggatacctgt ccgcctttct cccttcggga agcgtggcgc    720
tttctcatag ctcacgctgt aggtatctca gttcggtgta ggtcgttcgc tccaagctgg    780
gctgtgtgca cgaaccccc  gttcagcccg accgctgcgc cttatccggt aactatcgtc    840
ttgagaccaa cccggtaaga cacgacttat cgccactggc agcagccact ggtaacagga    900
ttagcagagc gaggtatgta ggcggtgcta cagagttctt gaagtggtgg cctaactacg    960
gctacactag aaggacagta tttggtatct gcgctctgct gaagccagtt accttcggaa   1020
aaagagttgg tagctcttga tccggcaaac aaaccaccgc tggtagcggt ggtttttttg   1080
tttgcaagca gcagattacg cgcagaaaaa aaggatctca agaagatcct ttgatctttt   1140
ctacggggtc tgacgctcag tggaacgaaa actcacgtta agggattttg gtcatgagat   1200
tatcaaaaag gatcttcacc tagatccttt taaattaaaa atgaagtttt aaatcaatct   1260
aaagtatata tgagtaaact tggtctgaca gttaccaatg cttaatcagt gaggcaccta   1320
tctcagcgat ctgtctattt cgttcatcca tagttgcctg actccccgtc gtgtagataa   1380
ctacgatacg ggagggctta ccatctggcc ccagtgctgc aatgataccg cgagacccac   1440
gctcaccggc tccagattta tcagcaataa accagccagc cggaagggcc gagcgcagaa   1500
gtggtcctgc aactttatcc gcctccatcc agtctattaa ttgttgccgg gaagctagag   1560
taagtagttc gccagttaat agtttgcgca acgttgttgg cattgctaca ggcatcgtgg   1620
tgtcacgctc gtcgtttggt atggcttcat tcagctccgg ttcccaacga tcaaggcgag   1680
ttacatgatc ccccatgttg tgcaaaaaag cggttagctc cttcggtcct ccgatcgttg   1740
tcagaagtaa gttggccgca gtgttatcac tcatggttat ggcagcactg cataattctc   1800
ttactgtcat gccatccgta agatgctttt ctgtgactgg tgagtactca accaagtcat   1860
tctgagaata gtgtatgcgg cgaccgagtt gctcttgccc ggcgtcaata cgggataata   1920
```

```
ccgcgccaca tagcagaact ttaaaagtgc tcatcattgg aaaacgttct tcggggcgaa      1980
aactctcaag gatcttaccg ctgttgagat ccagttcgat gtaacccact cgtgcaccca      2040
actgatcttc agcatctttt actttcacca gcgtttctgg gtgagcaaaa acaggaaggc      2100
aaaatgccgc aaaaaaggga ataagggcga cacggaaatg ttgaatactc atactcttcc      2160
tttttcaata ttattgaagc atttatcagg gttattgtct catgagcgga tacatatttg      2220
aatgtattta gaaaaataaa caaatagggg ttccgcgcac atttccccga aaagtgccac      2280
ctgacgtcta agaaaccatt attatcatga cattaaccta taaaaatagg cgtatcacga      2340
ggccctttcg tctcgcgcgt ttcggtgatg acggtgaaaa cctctgacac atgcagctcc      2400
cggagacggt cacagcttgt ctgtaagcgg atgccgggag cagacaagcc cgtcagggcg      2460
cgtcagcggg tgttggcggg tgtcggggct ggcttaacta tgcggcatca gagcagattg      2520
tactgagagt gcaccatatg cggtgtgaaa taccgcacag atgcgtaagg agaaaatacc      2580
gcatcaggcg ccattcgcca ttcaggctgc gcaactgttg ggaagggcga tcggtgcggg      2640
cctcttcgct attacgccag ctggcgaaag ggggatgtgc tgcaaggcga ttaagttggg      2700
taacgccagg gttttcccag tcacgacgtt gtaaaacgac ggccagtgaa ttgtaatacg      2760
actcactata                                                             2770
```

```
<210> SEQ ID NO 23
<211> LENGTH: 54
<212> TYPE: DNA
<213> ORGANISM: Artificial
<220> FEATURE:
<223> OTHER INFORMATION: oligonucleotide with homology to bacterial
      cloning vector

<400> SEQUENCE: 23
gcggccgcga ggagtatgga tccgactcga gtcggatcct ggctcctcgt cgac            54

<210> SEQ ID NO 24
<211> LENGTH: 26
<212> TYPE: DNA
<213> ORGANISM: Artificial
<220> FEATURE:
<223> OTHER INFORMATION: oligonucleotide with homology to bacterial
      cloning vector

<400> SEQUENCE: 24
gcggccgcga ggagtatgga tccgac                                           26

<210> SEQ ID NO 25
<211> LENGTH: 24
<212> TYPE: DNA
<213> ORGANISM: Artificial
<220> FEATURE:
<223> OTHER INFORMATION: oligonucleotide with homology to bacterial
      cloning vector

<400> SEQUENCE: 25
gtcggatcct ggctcctcgt cgac                                             24

<210> SEQ ID NO 26
<211> LENGTH: 10
<212> TYPE: DNA
<213> ORGANISM: mammalian
<220> FEATURE:
<221> NAME/KEY: polyA_site
<222> LOCATION: (1)..(10)

<400> SEQUENCE: 26
```

```
aaaaaaaaaa                                                                10

<210> SEQ ID NO 27
<211> LENGTH: 54
<212> TYPE: DNA
<213> ORGANISM: Artificial
<220> FEATURE:
<223> OTHER INFORMATION: oligonucleotide with homology to bacterial
      cloning vector

<400> SEQUENCE: 27
gcgcggcgct cctcatacct aggctgagct cagcctagga ccgaggagca gctg              54

<210> SEQ ID NO 28
<211> LENGTH: 26
<212> TYPE: DNA
<213> ORGANISM: Artificial
<220> FEATURE:
<223> OTHER INFORMATION: oligonucleotide with homology to bacterial
      cloning vector

<400> SEQUENCE: 28
cgccggcgct cctcatacct aggctg                                             26

<210> SEQ ID NO 29
<211> LENGTH: 24
<212> TYPE: DNA
<213> ORGANISM: Artificial
<220> FEATURE:
<223> OTHER INFORMATION: oligonucleotide with homology to bacterial
      cloning vector

<400> SEQUENCE: 29
cagcctagga ccgaggagca gctg                                               24
```